(12) United States Patent
Werther et al.

(10) Patent No.: US 7,829,319 B2
(45) Date of Patent: Nov. 9, 2010

(54) GLUTAMIC ACID-MODIFIED CLASSICAL SWINE FEVER VIRUS AUTOPROTEASES $N^{pro}$

(75) Inventors: Florian Werther, Innsbruck (AT); Clemens Achmüller, Innsbruck (AT); Philipp Wechner, Innsbruck (AT); Bernhard Auer, Innsbruck (AT); Silvio Podmirseg, Innsbruck (AT)

(73) Assignees: Sandoz AG, Basel (CH); Boehringer Ingelheim RCV GmbH & Co KG, Vienna (AT)

( * ) Notice: Subject to any disclaimer, the term of this patent is extended or adjusted under 35 U.S.C. 154(b) by 275 days.

(21) Appl. No.: 11/919,346

(22) PCT Filed: Apr. 25, 2006

(86) PCT No.: PCT/AT2006/000165

§ 371 (c)(1),
(2), (4) Date: Oct. 26, 2007

(87) PCT Pub. No.: WO2006/113957

PCT Pub. Date: Nov. 2, 2006

(65) Prior Publication Data

US 2010/0062490 A1  Mar. 11, 2010

(30) Foreign Application Priority Data

| Apr. 26, 2005 | (GB) | ................................. | 0508434.8 |
| Apr. 26, 2005 | (GB) | ................................. | 0508435.5 |
| Mar. 16, 2006 | (GB) | ................................. | 0605379.7 |

(51) Int. Cl.
| *C12N 9/50* | (2006.01) |
| *C12N 15/70* | (2006.01) |
| *C12N 15/74* | (2006.01) |
| *C12P 21/06* | (2006.01) |
| *C12N 15/57* | (2006.01) |
| *C12N 15/62* | (2006.01) |

(52) U.S. Cl. .................. 435/219; 435/69.1; 435/69.7; 435/252.3; 435/252.33; 435/320.1; 536/23.2; 536/23.4

(58) Field of Classification Search ........................ None
See application file for complete search history.

(56) References Cited

U.S. PATENT DOCUMENTS

| 6,936,455 | B1 * | 8/2005 | Stempfer et al. ............. 435/212 |
| 7,378,512 | B2 * | 5/2008 | Rumenapf et al. .......... 536/23.4 |
| 2009/0203069 | A1 * | 8/2009 | Jungbauer et al. .......... 435/69.1 |
| 2009/0306343 | A1 * | 12/2009 | Jungbauer et al. ........... 530/345 |

FOREIGN PATENT DOCUMENTS

| WO | WO-01/11056 A | 2/2001 |
| WO | WO-01/11057 A1 | 2/2001 |

OTHER PUBLICATIONS

Stark, R., et al., 1993, "Processing of pestivirus polyprotein: Cleavage site between autoprotease and nucleocapsid protein of classical swine fever virus", Journal of Virology, vol. 67, No. 12, pp. 7088-7095.*
Mishra, N., et al., 2006, "Genetic analysis of Indian bovine viral diarrhea virus 1 isolates in Npro and entire region coding structural proteins", Acta Virologica, vol. 50, No. 1, pp. 39-44.*
Gil, L. H. V. G., et al., 2006, "The amino-terminal domain of bovine viral diarrhea virus Npro protein is necessary for alpha/beta interferon antagonism", Journal of Virology, vol. 80, No. 2, pp. 900-911.*
Szymanski, M. R., et al., 2009, "Zinc binding in pestivirus Npro is required for interferon regulatory factor 3 interaction and degradation", Journal of Molecular Biology, vol. 391, No. 2, pp. 438-449.*
Hartl, Marcus et al., "JAC, a direct target of oncogenic transcription factor Jun, is involved in cell transformation and tumorigenesis", PNAS, Nov. 20, 2001, vol. 98, No. 24, pp. 13601-13606.
Ruemenapf Tillmann et al., "N-Terminal Protease of Pestiviruses: Identification of Putative Catalytic Residues by Site-Directed Mutagenesis", Journal of Virology, The American Society for Microbiology, vol. 72, No. 3, Mar. 1998, pp. 2544-2547.

* cited by examiner

*Primary Examiner*—Nashaat T Nashed
*Assistant Examiner*—William W Moore
(74) *Attorney, Agent, or Firm*—Birch, Stewart, Kolasch & Birch, LLP

(57) ABSTRACT

The invention relates to a process for the recombinant production of a heterologous polypeptide of interest by cultivating a bacterial host cell transformed with an expression vector comprising a nucleic acid molecule encoding a fusion polypeptide wherein (a) the amino-proximal fusion partner is an autoprotease $N^{pro}$ comprising the replacement(s) by glutamic acid of one or more cysteines at positions corresponding to the positions 112, 134, and 138 of the autoprotease $N^{pro}$ of classical swine fever virus and (b) the carboxyl-proximal fusion partner is an heterologous polypeptide of interest fused to the autoprotease $N^{pro}$ so that it is capable of being cleaved from the fusion polypeptide by autoprotease $N^{pro}$ autoproteolytic activity, said process comprising (i) cultivating the transformed host cell under conditions permitting the expression of the fusion polypeptide and the formation of corresponding cytoplasmic inclusion bodies, (ii) isolating the inclusion bodies from the host cell, (iii) solubilizing the isolated inclusion bodies, (iv) inducing autoproteolytic cleavage of the heterologous polypeptide of interest from the fusion polypeptide, and (v) isolating the cleaved heterologous polypeptide of interest.

26 Claims, No Drawings

SEQUENCE LISTING

<160> NUMBER OF SEQ ID NOS: 38

<210> SEQ ID NO 1
<211> LENGTH: 168
<212> TYPE: PRT
<213> ORGANISM: classical swine fever virus

<400> SEQUENCE: 1

Met Glu Leu Asn His Phe Glu Leu Leu Tyr Lys Thr Ser Lys Gln Lys
 1               5                  10                  15

```
Pro Val Gly Val Glu Glu Pro Val Tyr Asp Thr Ala Gly Arg Pro Leu
            20                  25                  30

Phe Gly Asn Pro Ser Glu Val His Pro Gln Ser Thr Leu Lys Leu Pro
            35                  40                  45

His Asp Arg Gly Arg Gly Asp Ile Arg Thr Thr Leu Arg Asp Leu Pro
        50                  55                  60

Arg Lys Gly Asp Cys Arg Ser Gly Asn His Leu Gly Pro Val Ser Gly
 65                 70                  75                  80

Ile Tyr Ile Lys Pro Gly Pro Val Tyr Tyr Gln Asp Tyr Thr Gly Pro
                85                  90                  95

Val Tyr His Arg Ala Pro Leu Glu Phe Phe Asp Glu Ala Gln Phe Cys
            100                 105                 110

Glu Val Thr Lys Arg Ile Gly Arg Val Thr Gly Ser Asp Gly Lys Leu
            115                 120                 125

Tyr His Ile Tyr Val Cys Val Asp Gly Cys Ile Leu Leu Lys Leu Ala
        130                 135                 140

Lys Arg Gly Thr Pro Arg Thr Leu Lys Trp Ile Arg Asn Phe Thr Asn
145                 150                 155                 160

Cys Pro Leu Trp Val Thr Ser Cys
                165

<210> SEQ ID NO 2
<211> LENGTH: 168
<212> TYPE: PRT
<213> ORGANISM: artificial
<220> FEATURE:
<223> OTHER INFORMATION: modified Npro of classical swine fever virus

<400> SEQUENCE: 2

Met Glu Leu Asn His Phe Glu Leu Leu Tyr Lys Thr Ser Lys Gln Lys
 1               5                  10                  15

Pro Val Gly Val Glu Glu Pro Val Tyr Asp Thr Ala Gly Arg Pro Leu
            20                  25                  30

Phe Gly Asn Pro Ser Glu Val His Pro Gln Ser Thr Leu Lys Leu Pro
            35                  40                  45

His Asp Arg Gly Arg Gly Asp Ile Arg Thr Thr Leu Arg Asp Leu Pro
        50                  55                  60

Arg Lys Gly Asp Cys Arg Ser Gly Asn His Leu Gly Pro Val Ser Gly
 65                 70                  75                  80

Ile Tyr Ile Lys Pro Gly Pro Val Tyr Tyr Gln Asp Tyr Thr Gly Pro
                85                  90                  95

Val Tyr His Arg Ala Pro Leu Glu Phe Phe Asp Glu Ala Gln Phe Glu
            100                 105                 110

Glu Val Thr Lys Arg Ile Gly Arg Val Thr Gly Ser Asp Gly Lys Leu
            115                 120                 125

Tyr His Ile Tyr Val Glu Val Asp Gly Glu Ile Leu Leu Lys Leu Ala
        130                 135                 140

Lys Arg Gly Thr Pro Arg Thr Leu Lys Trp Ile Arg Asn Phe Thr Asn
145                 150                 155                 160

Cys Pro Leu Trp Val Thr Ser Cys
                165

<210> SEQ ID NO 3
<211> LENGTH: 168
<212> TYPE: PRT
<213> ORGANISM: artificial
<220> FEATURE:
```

<223> OTHER INFORMATION: modified Npro of classical swine fever virus

<400> SEQUENCE: 3

```
Met Glu Leu Asn His Phe Glu Leu Leu Tyr Lys Thr Ser Lys Gln Lys
1               5                   10                  15

Pro Val Gly Val Glu Glu Pro Val Tyr Asp Thr Ala Gly Arg Pro Leu
            20                  25                  30

Phe Gly Asn Pro Ser Glu Val His Pro Gln Ser Thr Leu Lys Leu Pro
        35                  40                  45

His Asp Arg Gly Glu Asp Ile Glu Thr Thr Leu Arg Asp Leu Pro
    50                  55                  60

Arg Lys Gly Asp Cys Arg Ser Gly Asn His Leu Gly Pro Val Ser Gly
65                  70                  75                  80

Ile Tyr Ile Lys Pro Gly Pro Val Tyr Tyr Gln Asp Tyr Thr Gly Pro
                85                  90                  95

Val Tyr His Arg Ala Pro Leu Glu Phe Phe Asp Glu Ala Gln Phe Glu
            100                 105                 110

Glu Val Thr Lys Arg Ile Gly Arg Val Thr Gly Ser Asp Gly Lys Leu
        115                 120                 125

Tyr His Ile Tyr Val Glu Val Asp Gly Glu Ile Leu Leu Lys Gln Ala
    130                 135                 140

Lys Arg Gly Thr Pro Arg Thr Leu Lys Trp Ile Arg Asn Phe Thr Asn
145                 150                 155                 160

Cys Pro Leu Trp Val Thr Ser Cys
                165
```

<210> SEQ ID NO 4
<211> LENGTH: 168
<212> TYPE: PRT
<213> ORGANISM: artificial
<220> FEATURE:
<223> OTHER INFORMATION: modified Npro of classical swine fever virus

<400> SEQUENCE: 4

```
Met Glu Leu Asn His Phe Glu Leu Leu Tyr Lys Thr Ser Lys Gln Lys
1               5                   10                  15

Pro Val Gly Val Glu Glu Pro Val Tyr Asp Thr Ala Gly Arg Pro Leu
            20                  25                  30

Phe Gly Asn Pro Ser Glu Val His Pro Gln Ser Thr Leu Lys Leu Pro
        35                  40                  45

His Asp Arg Gly Arg Gly Asp Ile Arg Thr Thr Leu Arg Asp Leu Pro
    50                  55                  60

Arg Lys Gly Asp Cys Arg Ser Gly Asn His Leu Gly Pro Val Ser Gly
65                  70                  75                  80

Ile Tyr Ile Lys Pro Gly Pro Val Tyr Tyr Gln Asp Tyr Thr Gly Pro
                85                  90                  95

Val Tyr His Arg Ala Pro Leu Glu Phe Phe Asp Glu Thr Gln Phe Glu
            100                 105                 110

Glu Thr Thr Lys Arg Ile Gly Arg Val Thr Gly Ser Asp Gly Lys Leu
        115                 120                 125

Tyr His Ile Tyr Val Glu Val Asp Gly Glu Ile Leu Leu Lys Leu Ala
    130                 135                 140

Lys Arg Gly Thr Pro Arg Thr Leu Lys Trp Thr Arg Asn Thr Thr Asn
145                 150                 155                 160

Cys Pro Leu Trp Val Thr Ser Cys
                165
```

<210> SEQ ID NO 5
<211> LENGTH: 168
<212> TYPE: PRT
<213> ORGANISM: artificial
<220> FEATURE:
<223> OTHER INFORMATION: modified Npro of classical swine fever virus

<400> SEQUENCE: 5

Met Glu Leu Asn His Phe Glu Leu Leu Tyr Lys Thr Ser Lys Gln Lys
1               5                   10                  15

Pro Val Gly Val Glu Glu Pro Val Tyr Asp Thr Ala Gly Arg Pro Leu
            20                  25                  30

Phe Gly Asn Pro Ser Glu Val His Pro Gln Ser Thr Leu Lys Leu Pro
        35                  40                  45

His Asp Arg Gly Glu Asp Ile Glu Thr Thr Leu Arg Asp Leu Pro
    50                  55                  60

Arg Lys Gly Asp Cys Arg Ser Gly Asn His Leu Gly Pro Val Ser Gly
65                  70                  75                  80

Ile Tyr Ile Lys Pro Gly Pro Val Tyr Tyr Gln Asp Tyr Thr Gly Pro
                85                  90                  95

Val Tyr His Arg Ala Pro Leu Glu Phe Phe Asp Glu Thr Gln Phe Glu
            100                 105                 110

Glu Thr Thr Lys Arg Ile Gly Arg Val Thr Gly Ser Asp Gly Lys Leu
        115                 120                 125

Tyr His Ile Tyr Val Glu Val Asp Gly Glu Ile Leu Leu Lys Gln Ala
    130                 135                 140

Lys Arg Gly Thr Pro Arg Thr Leu Lys Trp Thr Arg Asn Thr Thr Asn
145                 150                 155                 160

Cys Pro Leu Trp Val Thr Ser Cys
                165

<210> SEQ ID NO 6
<211> LENGTH: 768
<212> TYPE: DNA
<213> ORGANISM: artificial
<220> FEATURE:
<223> OTHER INFORMATION: construct containing sequence for
      Npro-pro-insulin

<400> SEQUENCE: 6
atggaactca atcatttcga actgctctac aaaactagca agcaaaaacc tgttggcgtt      60
gaagagccgg tctacgatac tgcaggtcgt cctcttttg gaatccgtc cgaagtgcac       120 ccccagtcaa ccctcaagct tccccatgac cgcggacgcg gtgacattcg tacaacgctg      180
cgcgatctgc ctcgtaaagg cgattgtcgc tctggaaacc acctaggtcc ggtgtcgggc     240
atttacatta aaccaggtcc cgtctattac caagactaca ctggtccggt ttaccatcgt     300
gcacctctgg aattctttga tgaagctcaa ttttgcgaag tgactaaacg tattggccgt     360
gtaaccggtt cggacgggaa actgtaccac atctacgtgt gcgttgatgg ctgtatcctg     420
ctgaaactcg cgaagcgcgg aaccctcgc accctgaaat ggatccgtaa cttcactaac      480
tgtccactgt gggtcactag ttgcttcgtt aaccacatc tgtgcggttc acaccttgtg      540
gaagccctgt atctggtgtg tggcgaacgc ggattctttt ataccccgaa acgcggcgc      600 gaagccgaag atcttcaggt tggtcaagtg gaactgggcg gaggtccggg agccgggagc     660
ctgcaaccgc tggcgcttga agggtcgctg caaaaacgcg gtattgttga acagtgctgt     720

-continued acctccatct gctctctgta tcagctggaa aactactgca attaataa          768

<210> SEQ ID NO 7
<211> LENGTH: 26
<212> TYPE: DNA
<213> ORGANISM: artificial
<220> FEATURE:
<223> OTHER INFORMATION: primer

<400> SEQUENCE: 7
gctcaatttg aggaagtgac taaacg                                  26

<210> SEQ ID NO 8
<211> LENGTH: 26
<212> TYPE: DNA
<213> ORGANISM: artificial
<220> FEATURE:
<223> OTHER INFORMATION: primer

<400> SEQUENCE: 8
cgtttagtca cttcctcaaa ttgagc                                  26

<210> SEQ ID NO 9
<211> LENGTH: 22
<212> TYPE: DNA
<213> ORGANISM: artificial
<220> FEATURE:
<223> OTHER INFORMATION: primer

<400> SEQUENCE: 9
catctacgtg gaggttgatg gc                                      22

<210> SEQ ID NO 10
<211> LENGTH: 22
<212> TYPE: DNA
<213> ORGANISM: artificial
<220> FEATURE:
<223> OTHER INFORMATION: primer

<400> SEQUENCE: 10
gccatcaacc tccacgtaga tg                                      22

<210> SEQ ID NO 11
<211> LENGTH: 21
<212> TYPE: DNA
<213> ORGANISM: artificial
<220> FEATURE:
<223> OTHER INFORMATION: primer

<400> SEQUENCE: 11
gttgatggcg agatcctgct g                                       21

<210> SEQ ID NO 12
<211> LENGTH: 21
<212> TYPE: DNA
<213> ORGANISM: artificial
<220> FEATURE:
<223> OTHER INFORMATION: primer

<400> SEQUENCE: 12
cagcaggatc tcgccatcaa c                                       21

<210> SEQ ID NO 13
<211> LENGTH: 50
<212> TYPE: DNA
<213> ORGANISM: artificial

```
<220> FEATURE:
<223> OTHER INFORMATION: primer

<400> SEQUENCE: 13
ctggaattct tgatgaaac ccaatttgag gaaaccacta aacgtattgg                50

<210> SEQ ID NO 14
<211> LENGTH: 50
<212> TYPE: DNA
<213> ORGANISM: artificial
<220> FEATURE:
<223> OTHER INFORMATION: primer

<400> SEQUENCE: 14
ccaatacgtt tagtggtttc ctcaaattgg gtttcatcaa agaattccag               50

<210> SEQ ID NO 15
<211> LENGTH: 37
<212> TYPE: DNA
<213> ORGANISM: artificial
<220> FEATURE:
<223> OTHER INFORMATION: primer

<400> SEQUENCE: 15
catgaccgcg gagaagatga cattgaaaca acgctgc                            37

<210> SEQ ID NO 16
<211> LENGTH: 37
<212> TYPE: DNA
<213> ORGANISM: artificial
<220> FEATURE:
<223> OTHER INFORMATION: primer

<400> SEQUENCE: 16
gcagcgttgt ttcaatgtca tcttctccgc ggtcatg                            37

<210> SEQ ID NO 17
<211> LENGTH: 30
<212> TYPE: DNA
<213> ORGANISM: artificial
<220> FEATURE:
<223> OTHER INFORMATION: primer

<400> SEQUENCE: 17
gatcctgctg aaacaggcga agcgcggaac                                    30

<210> SEQ ID NO 18
<211> LENGTH: 30
<212> TYPE: DNA
<213> ORGANISM: artificial
<220> FEATURE:
<223> OTHER INFORMATION: primer

<400> SEQUENCE: 18
gttccgcgct tcgcctgttt cagcaggatc                                    30

<210> SEQ ID NO 19
<211> LENGTH: 52
<212> TYPE: DNA
<213> ORGANISM: artificial
<220> FEATURE:
<223> OTHER INFORMATION: primer

<400> SEQUENCE: 19
gcaactagtg acccacagtg gacagttagt ggtgttacgg gtccatttca gg           52
```

```
<210> SEQ ID NO 20
<211> LENGTH: 30
<212> TYPE: DNA
<213> ORGANISM: artificial
<220> FEATURE:
<223> OTHER INFORMATION: primer

<400> SEQUENCE: 20
cgcgacatat ggaactcaat catttcgaac                                       30

<210> SEQ ID NO 21
<211> LENGTH: 32
<212> TYPE: DNA
<213> ORGANISM: artificial
<220> FEATURE:
<223> OTHER INFORMATION: primer

<400> SEQUENCE: 21
cgcagagatg ttggtcgacg ctgcaactag tg                                    32

<210> SEQ ID NO 22
<211> LENGTH: 32
<212> TYPE: DNA
<213> ORGANISM: artificial
<220> FEATURE:
<223> OTHER INFORMATION: primer

<400> SEQUENCE: 22
ctttcgtcga cttattaatt gcagtagttt tc                                    32

<210> SEQ ID NO 23
<211> LENGTH: 52
<212> TYPE: DNA
<213> ORGANISM: artificial
<220> FEATURE:
<223> OTHER INFORMATION: primer

<400> SEQUENCE: 23
ctctcatatg catcaccatc atcatcacga actcaatcat ttcgaactgc tc              52

<210> SEQ ID NO 24
<211> LENGTH: 42
<212> TYPE: DNA
<213> ORGANISM: artificial
<220> FEATURE:
<223> OTHER INFORMATION: primer

<400> SEQUENCE: 24
gtaactagtt gcagcgatga cttcgttaac caacatctgt gc                         42

<210> SEQ ID NO 25
<211> LENGTH: 183
<212> TYPE: DNA
<213> ORGANISM: artificial
<220> FEATURE:
<223> OTHER INFORMATION: D of Staphylococcus aureus protein A

<400> SEQUENCE: 25
gcagacgcac aacagaataa gtttaacaaa gaccagcaga gcgcattcta cgaaattctg      60
aacatgccga atctgaatga ggaacaacgt aatggcttta ttcagtcttt aaaagacgac     120
ccatctcaga gcaccaacgt tctgggcgaa gcaaagaaac tgaacgaatc tcaggcacca     180
aaa                                                                  183
```

<210> SEQ ID NO 26
<211> LENGTH: 52
<212> TYPE: DNA
<213> ORGANISM: artificial
<220> FEATURE:
<223> OTHER INFORMATION: primer

<400> SEQUENCE: 26
atatactagt tgcgcagacg cacaacagaa taagtttaac aaagaccagc ag    52

<210> SEQ ID NO 27
<211> LENGTH: 50
<212> TYPE: DNA
<213> ORGANISM: artificial
<220> FEATURE:
<223> OTHER INFORMATION: primer

<400> SEQUENCE: 27
catgttcaga atttcgtaga atgcgctctg ctggtctttg ttaaacttat    50

<210> SEQ ID NO 28
<211> LENGTH: 50
<212> TYPE: DNA
<213> ORGANISM: artificial
<220> FEATURE:
<223> OTHER INFORMATION: primer

<400> SEQUENCE: 28
cattctacga aattctgaac atgccgaatc tgaatgagga acaacgtaat    50

<210> SEQ ID NO 29
<211> LENGTH: 50
<212> TYPE: DNA
<213> ORGANISM: artificial
<220> FEATURE:
<223> OTHER INFORMATION: primer

<400> SEQUENCE: 29
gggtcgtctt ttaaagactg aataaagcca ttacgttgtt cctcattcag    50

<210> SEQ ID NO 30
<211> LENGTH: 50
<212> TYPE: DNA
<213> ORGANISM: artificial
<220> FEATURE:
<223> OTHER INFORMATION: primer

<400> SEQUENCE: 30
tcagtcttta aaagacgacc catctcagag caccaacgtt ctgggcgaag    50

<210> SEQ ID NO 31
<211> LENGTH: 48
<212> TYPE: DNA
<213> ORGANISM: artificial
<220> FEATURE:
<223> OTHER INFORMATION: primer

<400> SEQUENCE: 31
ttttggtgcc tgagattcgt tcagtttctt tgcttcgccc agaacgtt    48

<210> SEQ ID NO 32
<211> LENGTH: 168
<212> TYPE: PRT
<213> ORGANISM: artificial
<220> FEATURE:
<223> OTHER INFORMATION: modified Npro of classical swine fever virus

<400> SEQUENCE: 32

```
Met Glu Leu Asn His Phe Glu Leu Leu Tyr Lys Thr Ser Lys Gln Lys
1               5                   10                  15

Pro Val Gly Val Glu Glu Pro Val Tyr Asp Thr Ala Gly Arg Pro Leu
            20                  25                  30

Phe Gly Thr Pro Ser Glu Val His Pro Gln Ser Thr Leu Lys Leu Pro
        35                  40                  45

His Asp Arg Gly Glu Asp Asp Ile Glu Thr Thr Leu Arg Asp Leu Pro
    50                  55                  60

Arg Lys Gly Asp Cys Arg Ser Gly Asn His Leu Gly Pro Val Ser Gly
65                  70                  75                  80

Ile Tyr Ile Lys Pro Gly Pro Val Tyr Tyr Gln Asp Tyr Thr Gly Pro
                85                  90                  95

Val Tyr His Arg Ala Pro Leu Glu Phe Phe Asp Glu Thr Gln Phe Glu
            100                 105                 110

Glu Thr Thr Lys Arg Ile Gly Arg Val Thr Gly Ser Asp Gly Lys Leu
        115                 120                 125

Tyr His Ile Tyr Val Glu Val Asp Gly Glu Ile Leu Leu Lys Gln Ala
    130                 135                 140

Lys Arg Gly Thr Pro Arg Thr Leu Lys Trp Thr Arg Asn Ser Thr Asn
145                 150                 155                 160

Cys Pro Leu Trp Val Thr Ser Cys
                165
```

<210> SEQ ID NO 33
<211> LENGTH: 168
<212> TYPE: PRT
<213> ORGANISM: artificial
<220> FEATURE:
<223> OTHER INFORMATION: modified Npro of classical swine fever virus

<400> SEQUENCE: 33

```
Met Glu Leu Asn His Phe Glu Leu Leu Tyr Lys Thr Ser Lys Gln Lys
1               5                   10                  15

Pro Val Gly Val Glu Glu Pro Val Tyr Asp Thr Glu Gly Arg Pro Leu
            20                  25                  30

Phe Gly Thr Pro Ser Glu Val His Pro Gln Ser Thr Leu Lys Leu Pro
        35                  40                  45

His Asp Arg Gly Glu Asp Asp Ile Glu Thr Thr Leu Arg Asp Leu Pro
    50                  55                  60

Arg Lys Gly Asp Cys Arg Phe Gly Asn His Leu Gly Pro Val Ser Gly
65                  70                  75                  80

Ile Tyr Ile Lys Pro Gly Pro Val Tyr Tyr Gln Asp Tyr Thr Gly Pro
                85                  90                  95

Val Tyr His Arg Ala Pro Leu Glu Phe Phe Asp Glu Thr Gln Phe Glu
            100                 105                 110

Glu Thr Thr Lys Arg Ile Gly Arg Val Thr Gly Ser Asp Gly Lys Leu
        115                 120                 125

Tyr His Ile Tyr Val Glu Val Asp Gly Glu Ile Leu Leu Lys Gln Ala
    130                 135                 140

Lys Arg Gly Thr Pro His Thr Leu Lys Trp Thr Arg Asn Ser Thr Asn
145                 150                 155                 160

Cys Pro Leu Trp Val Thr Ser Cys
                165
```

<210> SEQ ID NO 34
<211> LENGTH: 168
<212> TYPE: PRT
<213> ORGANISM: artificial
<220> FEATURE:
<223> OTHER INFORMATION: modified Npro of classical swine fever virus

<400> SEQUENCE: 34

Met Glu Leu Asn His Phe Glu Leu Leu Tyr Lys Thr Ser Lys Gln Lys
1               5                   10                  15

Pro Val Gly Val Glu Glu Pro Val Tyr Asp Thr Ala Gly Arg Pro Leu
            20                  25                  30

Phe Gly Asn Pro Ser Glu Val His Pro Gln Ser Thr Leu Lys Leu Pro
        35                  40                  45

His Asp Arg Gly Glu Asp Ile Glu Thr Thr Leu Arg Asp Leu Pro
    50                  55                  60

Arg Lys Gly Asp Cys Arg Ser Gly Asn His Leu Gly Pro Val Ser Gly
65                  70                  75                  80

Ile Tyr Ile Lys Pro Gly Pro Val Tyr Tyr Gln Asp Tyr Thr Gly Pro
                85                  90                  95

Val Tyr His Arg Ala Pro Leu Glu Phe Phe Asp Glu Ser Gln Phe Glu
            100                 105                 110

Glu Ser Thr Lys Arg Ile Gly Arg Val Thr Gly Ser Asp Gly Lys Leu
        115                 120                 125

Tyr His Ile Tyr Val Glu Val Asp Gly Glu Ile Leu Leu Lys Ser Ala
    130                 135                 140

Lys Arg Gly Thr Pro Arg Thr Leu Lys Trp Ser Arg Asn Ser Thr Asn
145                 150                 155                 160

Cys Pro Leu Trp Val Thr Ser Cys
                165

<210> SEQ ID NO 35
<211> LENGTH: 168
<212> TYPE: PRT
<213> ORGANISM: artificial
<220> FEATURE:
<223> OTHER INFORMATION: modified Npro of classical swine fever virus

<400> SEQUENCE: 35

Met Glu Leu Asn His Phe Glu Leu Leu Tyr Lys Thr Ser Lys Gln Lys
1               5                   10                  15

Pro Val Gly Val Glu Glu Pro Val Tyr Asp Thr Ala Gly Arg Pro Leu
            20                  25                  30

Phe Gly Asn Pro Ser Glu Val His Pro Gln Ser Thr Leu Lys Leu Pro
        35                  40                  45

His Asp Arg Gly Glu Asp Ile Glu Thr Thr Leu Arg Asp Leu Pro
    50                  55                  60

Arg Lys Gly Asp Cys Arg Ser Gly Asn His Leu Gly Pro Val Ser Gly
65                  70                  75                  80

Ile Tyr Ile Lys Pro Gly Pro Val Tyr Tyr Gln Asp Tyr Thr Gly Pro
                85                  90                  95

Val Tyr His Arg Ala Pro Leu Glu Phe Phe Asp Glu Ser Gln Phe Glu
            100                 105                 110

Glu Ser Thr Lys Arg Ile Gly Arg Val Thr Gly Ser Asp Gly Lys Leu
        115                 120                 125

Tyr His Ile Tyr Val Glu Val Asp Gly Glu Ile Leu Leu Lys Asn Ala
    130                 135                 140

```
Lys Arg Gly Thr Pro Arg Thr Leu Lys Trp Ser Arg Asn Ser Thr Asn
145                 150                 155                 160

Cys Pro Leu Trp Val Thr Ser Cys
            165

<210> SEQ ID NO 36
<211> LENGTH: 168
<212> TYPE: PRT
<213> ORGANISM: artificial
<220> FEATURE:
<223> OTHER INFORMATION: modified Npro of classical swine fever virus

<400> SEQUENCE: 36

Met Glu Leu Asn His Phe Glu Leu Leu Tyr Lys Thr Ser Lys Gln Lys
1               5                   10                  15

Pro Val Gly Val Glu Glu Pro Val Tyr Asp Thr Ala Gly Arg Pro Leu
            20                  25                  30

Phe Gly Asn Pro Ser Glu Val His Pro Gln Ser Thr Leu Lys Leu Pro
        35                  40                  45

His Asp Arg Gly Glu Asp Asp Ile Glu Thr Thr Leu Arg Asp Leu Pro
50                  55                  60

Arg Lys Gly Asp Cys Arg Ser Gly Asn His Leu Gly Pro Val Ser Gly
65                  70                  75                  80

Ile Tyr Ile Lys Pro Gly Pro Val Tyr Tyr Gln Asp Tyr Thr Gly Pro
                85                  90                  95

Val Tyr His Arg Ala Pro Leu Glu Phe Phe Asp Glu Ser Gln Phe Glu
            100                 105                 110

Glu Ser Thr Lys Arg Ile Gly Arg Val Thr Gly Ser Asp Gly Lys Leu
        115                 120                 125

Tyr His Ile Tyr Val Glu Val Asp Gly Glu Ile Leu Leu Lys Asp Ala
130                 135                 140

Lys Arg Gly Thr Pro Arg Thr Leu Lys Trp Ser Arg Asn Ser Thr Asn
145                 150                 155                 160

Cys Pro Leu Trp Val Thr Ser Cys
            165

<210> SEQ ID NO 37
<211> LENGTH: 168
<212> TYPE: PRT
<213> ORGANISM: artificial
<220> FEATURE:
<223> OTHER INFORMATION: modified Npro of classical swine fever virus

<400> SEQUENCE: 37

Met Glu Leu Asn His Phe Glu Leu Leu Tyr Lys Thr Ser Lys Gln Lys
1               5                   10                  15

Pro Val Gly Val Glu Glu Pro Val Tyr Asp Thr Ala Gly Arg Pro Leu
            20                  25                  30

Phe Gly Asn Pro Ser Glu Val His Pro Gln Ser Thr Leu Lys Leu Pro
        35                  40                  45

His Asp Arg Gly Glu Asp Asp Ile Glu Thr Thr Leu Arg Asp Leu Pro
50                  55                  60

Arg Lys Gly Asp Cys Arg Ser Gly Asn His Leu Gly Pro Val Ser Gly
65                  70                  75                  80

Ile Tyr Ile Lys Pro Gly Pro Val Tyr Tyr Gln Asp Tyr Thr Gly Pro
                85                  90                  95

Val Tyr His Arg Ala Pro Leu Glu Phe Phe Asp Glu Ser Gln Phe Glu
            100                 105                 110
```

```
Glu Ser Thr Lys Arg Ile Gly Arg Val Thr Gly Ser Asp Gly Lys Leu
            115                 120                 125

Tyr His Ile Tyr Val Glu Val Asp Gly Glu Ile Leu Leu Lys His Ala
            130                 135                 140

Lys Arg Gly Thr Pro Arg Thr Leu Lys Trp Ser Arg Asn Ser Thr Asn
145                 150                 155                 160

Cys Pro Leu Trp Val Thr Ser Cys
                165

<210> SEQ ID NO 38
<211> LENGTH: 168
<212> TYPE: PRT
<213> ORGANISM: artificial
<220> FEATURE:
<223> OTHER INFORMATION: modified Npro of classical swine fever virus

<400> SEQUENCE: 38

Met Glu Leu Asn His Phe Glu Leu Leu Tyr Lys Thr Ser Lys Gln Lys
1               5                   10                  15

Pro Val Gly Val Glu Glu Pro Val Tyr Asp Thr Ala Gly Arg Pro Leu
            20                  25                  30

Phe Gly Asn Pro Ser Glu Val His Pro Gln Ser Thr Leu Lys Leu Pro
            35                  40                  45

His Asp Arg Gly Glu Asp Asp Ile Glu Thr Thr Leu Arg Asp Leu Pro
        50                  55                  60

Arg Lys Gly Asp Cys Arg Ser Gly Asn His Leu Gly Pro Val Ser Gly
65                  70                  75                  80

Ile Tyr Ile Lys Pro Gly Pro Val Tyr Tyr Gln Asp Tyr Thr Gly Pro
                85                  90                  95

Val Tyr His Arg Ala Pro Leu Glu Phe Phe Asp Glu Ser Gln Phe Glu
            100                 105                 110

Glu Ser Thr Lys Arg Ile Gly Cys Val Thr Gly Ser Asp Gly Lys Leu
            115                 120                 125

Tyr His Ile Tyr Val Glu Val Asp Gly Glu Ile Leu Leu Lys Gln Ala
            130                 135                 140

Lys Arg Gly Thr Pro Arg Thr Leu Lys Trp Ser Arg Asn Ser Thr Asn
145                 150                 155                 160

Cys Pro Leu Trp Val Thr Ser Cys
                165
```

GLUTAMIC ACID-MODIFIED CLASSICAL SWINE FEVER VIRUS AUTOPROTEASES N$^{pro}$

FIELD OF INVENTION

The present Invention relates to a process for the recombinant production of a desired heterologous polypeptide of Interest with a dearly defined homogeneous N-terminus in a bacterial host cell, wherein initially a fusion polypeptide which comprises a derivative of the autoprotease N$^{pro}$ of Pestivirus and the heterologous polypeptide of interest is provided by expression in a host cell. The heterologous polypeptide of interest is produced in the host cell in form of cytoplasmic inclusion bodies, which are then isolated and treated in such a way, that the desired heterologous polypeptide is cleaved from the fusion polypeptide by the N$^{pro}$ autoproteolytic activity.

BACKGROUND OF INVENTION

In the production of recombinant proteins in heterologous organisms such as the expression of human or other eukaryotic proteins in bacterial cells it is often difficult to obtain a clearly defined N-terminus which is as nearly 100% homogeneous as possible. This apples in particular to recombinant pharmaceutical proteins whose amino add sequence in many cases ought to be identical to the amino acid sequence naturally occurring in humans/animals.

On natural expression, for example in humans, many pharmaceutical proteins which are in use for therapy as well are transported into the extracellular space. A signal sequence is present in the precursor protein for this purpose and cleavage of this signal sequence results in a clearly defined N-terminus. For several reasons such homogeneous N-termini are not always easy to produce, for example in bacterial cells.

For production on industrial scale, many pharmaceutical proteins are produced in the cytoplasm of bacterial cells (for example *Escherichia coli*). In the host cells the pharmaceutical proteins are accumulated in adequate quantities and are often deposited as Insoluble inclusion bodies (IBs) inside the cell. These IBs have great advantages in working up and purification of the target protein. In addition, the protein expressed in the form of IBs is protected from protease degradation by intacellular proteases.

As used herein the term "inclusion bodies" shall refer to aggregates containing heterologous polypeptides present in the cytoplasm of transformed host cells. These appear as bright spots under the microscope and can be recovered by separation of the cytoplasm.

However, production of IB material requires in vitro refolding of the expressed protein. This can in many cases be effected by methods known per se.

Only in rare cases is export of the target protein into the bacterial periplasm with the aid of a pro or eukaryotic signal sequence suitable. Because of the low transport capacity of the bacterial export machinery it is usually only possible to accumulate very small quantities of product here.

However, the bacterial cytoplasm differs considerably from the extracellular space of eukaryotes. One difference is that within the bacterial cytoplasm reducing conditions are predominant, also a mechanism for cleaving N-terminal leader sequences to form mature proteins is lacking. Synthesis of all cytoplasmic proteins starts with a methionine which is specified by the appropriate start codon (ATG=initiation of translation). This N-terminal methionine is retained in many proteins, while in others it is cleaved by the methionine aminopeptidase (MAP) present in the cytoplasm and intrinsic to the host. The efficiency of the cleavage depends essentially on two parameters: 1. the nature of the following amino acid, and 2. the location of the N-terminus in the three-dimensional structure of the protein. The N-terminal methionine is preferentially deleted when the following amino acid is serine, alanine, glycine, methionine or valine and when the N-terminus is exposed, i.e. not "hidden" inside the protein. If the following amino acid is a different one, in particular a charged one (glutamic acid, aspartic acid, lysine, arginine), or if the N-terminus is located inside the protein, in most cases cleavage of the N-terminal methionine does not occur.

Even if an amino acid that promotes cleavage is present at position 2, the cleavage is rarely complete. It is usual for a not inconsiderable portion (1-60%) of the target protein to remain unaffected by the MAP.

This in-homogenelty or deviation from the natural sequence is, however, unacceptable in many cases because these products frequently show different immunological (for example induction of antibody formation) and pharmacological (half-life, pharmacokinetics) properties. For these reasons, it is necessary in most cases to produce a nature-identical product (homogeneous and without foreign amino acids at the N-terminus). In the case of cytoplasmic expression, the remedy here in most cases is to fuse a cleavage sequence (leader) for a specific endopeptidase (for example factor Xa, enterokinase, KEX endopeptidases, IgA protease) or aminopeptidase (for example dipeptidyl aminopeptidase) to the N-terminus of the target protein. However, this makes an additional step necessary during further working up, the so called down stream processing of the protein, with expenditure of costs and materials. In addition, in the presence of IBs there is in many cases interference with or even complete prevention of the refolding by the leader sequence.

Fusion polypeptides comprising the autoprotease N$^{pro}$ of Pestivirus are especially useful in this respect. The autoprotease N$^{pro}$ of Pestivirus always cleaves off the fusion partner at a clearly determined site, releasing a polypeptide of interest with homogenous N-terminus. In addition, the autoproteolytic activity of N$^{pro}$ can be induced in vitro, by application of special buffers, so that the polypeptide of interest can be obtained by cleavage of fusion polypeptides that are expressed in IBs.

Pestiviruses are small enveloped viruses with a genome which acts directly as mRNA and is 12.3 kb in size and from which the viral gene products are transcribed in the cytoplasm. This takes place in the form of a single polyprotein which comprises about 4000 amino acids and which is broken down both by viral and by cellular proteases into about 12 mature proteins.

Pestiviruses comprise the subclasses CSFV (classical swine fever virus), BDV (border disease virus) and BVDV (bovine viral diarrhoea virus).

N$^{pro}$ is an autoprotease with a length of 168 amino acids and an apparent $M_r$ of about 20,000 (in vivo). It is the first protein in the polyprotein of Pestiviruses and undergoes autoproteolytic cleavage from the following nucleocapsid protein C. This cleavage takes place after the lest amino add in the sequence of N$^{pro}$, Cys168.

Use of the naturally occurring autoprotease N$^{pro}$ of Pestivirus for production of heterologous polypeptides of interest may be limited though, as activation of autoproteolytic function of N$^{pro}$ in vitro is susceptible only to specific renaturazing conditions. These conditions that allow for the cleavage activity of N$^{pro}$ in vitro are inhibitory for certain other interactions which are necessary or desirable in some settings for production of heterologous polypeptides of interest. As an example of such interactions certain bio-specific affinities as e.g. selective peptide-protein affinity can be named. Also, due to other requirements of parameters, certain processes do not permit to create the favourable renaturazing conditions for N$^{pro}$ and as a result N$^{pro}$ can not be used in these processes. Therefore the naturally occurring N$^{pro}$ of Pestivirus may be unsuitable for the production of certain polypeptides of interest and for use under certain conditions. Accordingly the need for an N$^{pro}$ of Pestivirus with improved properties exists, in order to enhance cleavage efficiency, to obtain higher yields of polypeptide of interest, and in order to be able to use N$^{pro}$ in a wider range of conditions, which allow for the application of new production processes.

SUMMARY OF INVENTION

Within the present invention it has surprisingly been found, that certain derivatives of the naturally occurring autoprotease N$^{pro}$ of Pestivirus, which have a lower pi and enhanced solubility are suitable for use in a wider range of conditions. In addition these derivatives were surprisingly found to have improved autoproteolytic activity in vitro.

Accordingly within the scope of the present invention an improved process for the production of heterologous polypeptides of interest with homogenous N-termini is provided, which makes use of the derivatives of autoprotease N$^{pro}$ of Pestivirus, also part of the present invention.

DETAILED DESCRIPTION OF INVENTION

The present invention relates to a process for the recombinant production of a heterologous polypeptide of interest comprising (i) cultivation of a bacterial host cell which is transformed with an expression vector which comprises a nucleic acid molecule which codes for a fusion polypeptide, the fusion polypeptide comprising a derivative of an autoprotease N$^{pro}$ of Pestivirus, wherein at least one cysteine residue of the naturally occuring autoprotease N$^{pro}$ of Pestivirus is replaced by another amino acid residue, and a second polypeptide, which is connected to the derivative at the C-terminus of the derivative in a manner such, that the second polypeptide is capable of being cleaved from the fusion polypeptide by the autoproteolytic activity of the derivative, and the second polypeptide being a heterologous polypeptide, wherein cultivation occurs under conditions which cause expression of the fusion polypeptide and formation of corresponding cytoplasmic inclusion bodies, (ii) isolation of the inclusion bodies from the host cell,
(iii) solubilization of the isolated inclusion bodies,
(iv) induction of autoproteolytic cleavage of the heterologous polypeptide from the fusion polypeptide, and
(v) isolation of the cleaved heterologous polypeptide.

A preferred autoprotease N$^{pro}$ of pestivirus from which a derivative according to the present invention is derived, is the autoprotease N$^{pro}$ of CSFV, having the following amino acid sequence:

SEQ ID NO 1:
(1)-MELNHFELLYKTSKQKPVGVEEPVYDTAGRPLFGNPSEVHPQSTLK

LPHDRGRGDIRTTLRDLPRKGDCRSGNHLGPVSGIYIKPGPVYYQDYTGP

VYHRAPLEFFDEAQFCEVTKRIGRVTGSDGKLYHIYVCVDGCILLKLAKR

GTPRTLKWIRNFTNCPLWVTSC-(168)

Within the present invention the above sequence is mutated in order to generate fusion polypeptides with improved properties, the fusion polypeptides comprising a derivative of an autoprotease N$^{pro}$ of Pestivirus, wherein at least one cysteine residue of the naturally occuring autoprotease N$^{pro}$ of Pestivirus is replaced by another amino acid residue, and a second polypeptide, which is connected to said derivative at its C-terminus in a manner such, that the second polypeptide is capable of being cleaved from the fusion polypeptide by the autoproteolytic activity of the autoprotease derivative, said second polypeptide being a heterologous polypeptide.

Accordingly, the present invention relates to such derivatives of the naturally occurring N$^{pro}$ of Pestivirus, which are used in be process of the present invention as N-terminal part of the fusion protein. The derivatives are part of the invention in the sense that they are part of the fusion protein used within the process for the production of heterologous proteins, to which the present invention also relates.

In another aspect the present invention relates to derivatives of the naturally occurring N$^{pro}$ Pestivirus, which have reduced tendency to aggregate.

Within the present invention such derivatives of the naturally occuring N$^{pro}$ of Pestivirus are preferred, wherein the number of cysteine residues is reduced.

Within the present invention derivatives of the naturally occurring N$^{pro}$ of CSFV are particularly preferred.

Accordingly the present invention relates to a derivative of an autoprotease N$^{pro}$ of CSFV, wherein at least one cysteine residue of the naturally occuring autoprotease N$^{pro}$ of CSFV is replaced by another amino acid residue.

Thus the present invention also relates in another aspect to a press as described above, wherein the fusion polypeptide comprises a derivative of an autoprotease N$^{pro}$ of CSFV, wherein at least one cysteine residue of the naturally occuring autoprotease N$^{pro}$ of CSFV is replaced by another amino acid residue.

Preferably the present invention relates to a derivative of an autoprotease N$^{pro}$ of CSFV, wherein at least one cysteine residue of the naturally occuring autoprotease N$^{pro}$ of CSFV selected from the group consisting of C112, C134 and C138, is replaced by another amino add residue.

Thus in another aspect the present invention preferably relates to a process as described above, wherein the fusion polypeptide comprises a derivative of an autoprotease N$^{pro}$ of CSFV, wherein at least one cysteine residue of the naturally occuring autoprotease N$^{pro}$ of CSFV, selected from the group consisting of C112, C134 and C138, is replaced by a another amino acid residue.

Even further preference is given to a derivative of an autoprotease N$^{pro}$ of CSFV, wherein at least one cysteine residue of the naturally occuring autoprotease N$^{pro}$ of CSFV selected from the group consisting of C112, C134 and C138, is replaced by a glutamic acid residue.

Thus in another aspect the present invention more preferably relates to a process as described above, wherein the fusion polypeptide comprises a derivative of an autoprotease N$^{pro}$ of CSFV, wherein at least one cysteine residue of the naturally occuring autoprotease N$^{pro}$ of CSFV, selected from the group consisting of C112, C134 and C138, is replaced by a glutamic acid residue.

Further preference is given to a derivative of the autoprotease N$^{pro}$ of CSFV comprising the following amino acid sequence:

SEQ ID NO 2:
(1)-MELNHFELLYKTSKQKPVGVEEPVYDTAGRPLFGNPSEVHPQSTLK

LPHDRGRGDIRTTLRDLPRKGDCRSGNHLGPVSGIYIKPGPVYYQDYTGP

VYHRAPLEFFDEAQFEEVTKRIGRVTGSDGKLYHIYVEVDGEILLKLAKR

GTPRTLKWIRNFTNCPLWVTSC-(168)

Thus in another aspect the present invention relates with further preference to a process as described above, wherein the fusion polypeptide comprises a derivative of an autoprotease N$^{pro}$ of CSFV having a sequence according to SEQ ID NO 2.

Solubility of the derivatives is determined in the following way:

After 72 hours a concentrated solution of the respective N$^{pro}$ derivative is centrifuged, the pellet dissolved and applied to SDS gel-electrophoresis. A part of the supernatant is combined with probe buffer and applied to SDS gel-electrophoresis. After electrophoresis the bands are stained with coomassie blue, quantified by densitometry with an AlphaDigiDoc™ system and the amount of precipitated material is calculated. For experimental details see example 2.

Ionic strength of the buffer is often limiting to certain production processes. Therefore the present invention relates in a further aspect to derivatives of the naturally occurring N$^{pro}$ of Pestivirus, which have a more neutral pI than the naturally occurring N$^{pro}$ of Pestivirus. It is preferred to adapt the pI of the N$^{pro}$ of Pestivirus moiety of the fusion polypeptide to be expressed as close as feasible to the pI of the second polypeptide (the polypeptide of interest). For example, the N$^{pro}$ of Pestivirus moiety of the fusion polypeptide may have a pI of from 5.5 to 9.5, especially from 6.0 to 9.0.

Accordingly, within the present invention further preference is given to a derivative of an autoprotease N$^{pro}$ of CSFV, wherein in addition to the replacement of at least one cysteine residue as described above, at least one basic amino acid residue is replaced by an acidic amino acid residue.

Thus in another aspect the present invention relates with further preference to a process as described above, wherein the fusion polypeptide comprises a derivative of an autoprotease N$^{pro}$ of CSFV, wherein in addition to the replacement of at least one cysteine residue as described above, at least one basic amino acid residue is replaced by an acidic amino acid residue.

Further preference is given to a derivative of an autoprotease N$^{pro}$ of CSFV, wherein in addition to the replacement of at least one cysteine residue as described above, furthermore, at least one of the following amino acids are exchanged: H5, K16, N35, R53, G54, R57, L143, K145 and R150. A preferred example is a derivative wherein the following amino acids are exchanged: arginine (R) 53 with glutamic acid (E), glycine (G) 54 with aspartic acid (D), arginine (R) 57 with glutamic add (E), and leucine (L) 143 with glutamine (Q).

Thus in another aspect the present invention relates with further preference to a process as described above, wherein the fusion polypeptide comprises a derivative of an autoprotease N$^{pro}$ of CSFV, wherein in addition to the replacement of at least one cysteine residue as described above, the following amino acids are exchanged: arginine (R) 53 with glutamic acid (E), glycine (G) 54 with aspartic acid (D), arginine (R) 57 with glutamic acid (E), and leucine (L) 143 with glutamine (Q).

In another preferred embodiment of the present invention a derivative of the autoprotease N$^{pro}$ of CSFV comprises the following amino acid sequence.

SEQ ID NO 3:
(1)-MELNHFELLYKTSKQKPVGVEEPVYDTAGRPLFGNPSEVHPQSTLK

LPHDRGEDDIETTLRDLPRKGDCRSGNHLGPVSGIYIKPGPVYYQDYTGP

VYHRAPLEFFDEAQFEEVTKRIGRVTGSDGKLYHIYVEVDGEILLKQAKR

GTPRTLKWIRNFTNCPLWVTSC- (168) .

Thus in another aspect the present invention also relates to a process as described above, wherein the fusion polypeptide comprises a derivative of an autoprotease N$^{pro}$ of CSFV having a sequence according to SEQ ID NO 3.

In jet another aspect the present invention relates to a derivative of the naturally occurring N$^{pro}$ of a Pestivirus, which shows in addition to the reduced aggregation and more neutral pI further enhanced solubility, as compared to the naturally occurring N$^{pro}$ of a Pestivirus.

Solubility is determined as described above.

Accordingly the present invention relates to a derivative of an autoprotease N$^{pro}$ of CSFV, wherein, in addition to the replacement of at least one cysteine residue as described above, at least one hydrophobic amino acid residue is replaced by a hydrophilic residue.

Thus in another aspect the present invention also relates to a process as described above, wherein the fusion polypeptide comprises a derivative of an autoprotease N$^{pro}$ of CSFV, wherein in addition to the replacement of at least one cysteine residue as described above, at least one hydrophobic amino acid residue is replaced by a hydrophilic residue.

Preferred within the present invention is a derivative of an autoprotease N$^{pro}$ of CSFV, wherein in addition to the replacement of at least one cysteine residue as described above furthermore at least one of the following amino acids are replaced: V24, A27, L32, G54, L75, A109, V114, V121, L143, I155 and F158. A preferred example is a derivative wherein the following amino acids are exchanged by threonine (T): alanine (A) 109, valine (V) 114, Isoleucine (I) 155 and phenylalanine (F)158.

Thus in another aspect the present invention relates preferably to a process as described above, wherein the fusion polypeptide comprises a derivative of an autoprotease N$^{pro}$ of CSFV, wherein in addition to the replacement of at least one cysteine residue as described above, the following amino acids are replaced by threonine (T): alanine (A) 109, valine (V) 114, isoleucine (I)155 and phenylalanine (F)158. Another, within the present invention more preferred derivative of an autoprotease N$^{pro}$ of CSFV, comprises the following amino acid sequence:

SEQ ID NO 4:
(1)-MELNHFELLYKTSKQKPVGVEEPVYDTAGRPLFGNPSEVHPQSTLK

LPHDRGRGDIRTTLRDLPRKGDCRSGNHLGPVSGIYIKPGPVYYQDYTGP

VYHRAPLEFFDETQFEETTKRIGRVTGSDGKLYHIYVEVDGEILLKLAKR

GTPRTLKWTRNTTNCPLWVTSC- (168)

Thus in another aspect the present invention more preferably relates to a process as described above, wherein the fusion polypeptide comprises a derivative of an autoprotease N$^{pro}$ of CSFV having a sequence according to SEQ ID NO 4.

Even more preferred within the present invention is a derivative of an autoprotease N$^{pro}$ of CSFV, wherein in addition to the replacement of at least one cysteine residue as described above the following amino acids have been exchanged: alanine (A) 109, valine (V) 114, isoleucine (I) 155 and phenylalanine (F) 158 by threonine (T), arginine (R) 53 with glutamic acid (E), glycine (G) 54 with aspartic acid (D), arginine (R) 57 with glutamic add (E), and leucine (L) 143 with glutamine (Q).

Thus in another aspect the present invention relates even more preferably to a process as described above, wherein the fusion polypeptide comprises a derivative of an autoprotease N$^{pro}$ of CSFV, wherein in addition to the replacement of at least one cysteine residue as described above the following amino acids have been exchanged: alanine (A) 109, valine (V) 114, isoleucine (I) 155 and phenylalanine (F) 158 by threonine (T); arginine (R) 53 with glutamic acid (E), glycine (G) 54 with aspartic acid (D), arginine (R) 57 with glutamic acid (E), and leucine (L) 143 with glutamine (Q).

Most preferably the derivative of an autoprotease N$^{pro}$ of CSFV according to the present invention comprises the following amino acid sequence:

```
SEQ ID NO 5:
(1)-MELNHFELLYKTSKQKPVGVEEPVYDTAGRPLFGNPSEVHPQSTLK

LPHDRGEGDIETTLRDLPRKGDCRSGNHLGPVSGIYIKPGPVYYQDYTGP

VYHRAPLEFFDETQFEETTKRIGRVTGSDGKLYHIYVEVDGEILLKQAKR

GTPRTLKWTRNTTNCPLWVTSC-(168)
```

Thus in another, most preferred aspect the present invention also relates to a process as described above, wherein the fusion polypeptide comprises a derivative of an autoprotease N$^{pro}$ of CSFV having a sequence according to SEQ ID NO 5.

In another equally preferred aspect the present invention relates to a process for the production of heterologous proteins as described above, wherein the fusion polypeptide comprises a derivative of an autoprotease N$^{pro}$ of CSFV having a sequence according to SEQ. ID NO. 5, wherein in addition asparagine (N) 35 is replaced with threonine (T), and threonine (T) 158 is replaced with serine (S).

The derivative of an autoprotease N$^{pro}$ of CSFV which is utilized in the process according to the above aspect of the present invention forms also part of the present invention and comprises the following amino add sequence:

```
SEQ ID NO 32:
(1)-MELNHFELLYKTSKQKPVGVEEPVYDTAGRPLFGTPSEVHPQSTLK

LPHDRGEGDIETTLRDLPRKGDCRSGNHLGPVSGIYIKPGPVYYQDYTGP

VYHRAPLEFFDETQFEETTKRIGRVTGSDGKLYHIYVEVDGEILLKQAKR

GTPRTLKWTRNSTNCPLWVTSC-(168).
```

In another preferred aspect the present invention relates to a process for the production of heterologous proteins as described above, wherein the fusion polypeptide comprises a derivative of an autoprotease N$^{pro}$ of CSFV having a sequence according to SEQ. ID NO. 32, wherein in addition alanine (a) 28 is replaced with glutamic acid (E), serine (S) 71 is replaced with phenylalanine (F) and arginine (R) 150 is replaced with histidine (H).

The derivative of an autoprotease N$^{pro}$ of CSFV which is utilized in the process according the above aspect of the present invention forms also part of the present invention and comprises the following amino acid sequence:

```
SEQ ID NO 33:
(1)-MELNHFELLYKTSKQKPVGVEEPVYDTEGRPLFGNPSEVHPQSTLK

LPHDRGEDDIETTLRDLPRKGDCRSGNHLGPVSGIYIKPGPVYYQDYTGP

VYHRAPLEFFDETQFEETTKRIGRVTGSDGKLYHIYVEVDGEILLKQAKR

GTPHTLKWTRNSTNCPLWVTSC-(168).
```

Preferably in the process according to the present invention the derivative of an autoprotease N$^{pro}$ of CSFV with the sequence according to SEQ ID NO 32 is used in fusion with a protein that contains at least the three first amino acids of proinsulin, more preferably with proinsulin, further more preferably with human proinsulin, most preferably with recombinant human proinsulin, for the production of proinsulin.

It is preferred according to the present invention if the derivative of an autoprotease N$^{pro}$ of CSFV has in addition to the replacement of at least one cysteine residue as described above at least one of the following amino acids exchanged: arginine (R) 53, glycine (G) 54, arginine (R) 57, threonine (T) 109, 114, 155, 158 and leucine (L) 143. Preferred derivatives of the autoprotease N$^{pro}$ of CSFV according to the present invention have in addition to the replacement of at least one cysteine residue as described above, the following amino acids are exchanged: arginine (R) 53 with glutamic acid (E), glycine (G) 54 with aspartic acid (D), arginine (R) 57 with glutamic acid (E), threonine (T) 109, 114, 155, 158 with serine (S) and leucine (L) 143 with glutamine (Q) or asparagine (N) or aspartic add (D) or serine (S) or histidine:

Such preferred derivatives of an autoprotease N$^{pro}$ of CSFV which are utilized in the process according the above aspect of the present invention forms also part of the present invention and comprise the following amino acid sequences:

```
SEQ ID 92:
(1)-MELNHFELLYKTSKQKPVGVEEPVYDTAGRPLFGNPSEVHPQSTLK

LPHDRGEDDIETTLRDLPRKGDCRSGNHLGPVSGIYIKPGPVYYQDYTGP

VYHRAPLEFFDESQFEESTKRIGRVTGSDGKLYHIYVEVDGEILLKSAKR

GTPRTLKWSRNSTNCPLWVTSC-(168).

SEQ ID 95:
(1)-MELNHFELLYKTSKQKPVGVEEPVYDTAGRPLFGNPSEVHPQSTLK

LPHDRGEDDIETTLRDLPRKGDCRSGNHLGPVSGIYIKPGPVYYQDYTGP

VYHRAPLEFFDESQFEESTKRIGRVTGSDGKLYHIYVEVDGEILLKNAKR

GTPRTLKWSRNSTNCPLWVTSC-(168).

SEQ ID 96:
(1)-MELNHFELLYKTSKQKPVGVEEPVYDTAGRPLFGNPSEVHPQSTLK

LPHDRGEDDIETTLRDLPRKGDCRSGNHLGPVSGIYIKPGPVYYQDYTGP

VYHRAPLEFFDESQFEESTKRIGRVTGSDGKLYHIYVEVDGEILLKDAKR

GTPRTLKWSRNSTNCPLWVTSC-(168).

SEQ ID 97:
(1)-MELNHFELLYKTSKQKPVGVEEPVYDTAGRPLFGNPSEVHPQSTLK

LPHDRGEDDIETTLRDLPRKGDCRSGNHLGPVSGIYIKPGPVYYQDYTGP

VYHRAPLEFFDESQFEESTKRIGRVTGSDGKLYHIYVEVDGEILLKHAKR

GTPRTLKWSRNSTNCPLWVTSC-(168).

SEQ ID 98:
(1)-MELNHFELLYKTSKQKPVGVEEPVYDTAGRPLFGNPSEVHPQSTLK

LPHDRGEDDIETTLRDLPRKGDCRSGNHLGPVSGIYIKPGPVYYQDYTGP

VYHRAPLEFFDESQFEESTKRIGCVTGSDGKLYHIYVEVDGEILLKQAKR

GTPRTLKWSRNSTNCPLWVTSC-(168).
```

The derivatives of the naturally occurring N$^{pro}$ of CSFV described above which are part of the present invention, have improved properties over the naturally occurring N$^{pro}$ of CSFV and are therefore suitable to enhance efficiency of protein production. Refolding of the derivatives described in this invention can be induced in vitro in a wide range of conditions, e.g. under lower ionic strengths, where the natural occurring N$^{pro}$ would by dysfunctional. Therefore the derivates described above are suitable for use under reaction conditions that do not allow for successful use of the naturally occurring $N^{pro}$. The derivatives which are last described herein is particularly preferred within the present invention, due to its suitability for use in a particularly wide range of reaction conditions.

In a further aspect the present invention relates to the use of any of the derivatives of an autoprotease $N^{pro}$ of CSFV described above in a process for the production of heterologous polypeptides of interest according to the present invention.

Thus in the process for recombinant production of heterologous polypeptides of interest according to the present invention, the fusion polypeptide comprises any one of the above described derivatives of an autoprotease $N^{pro}$ of CSFV.

In a preferred embodiment of the present invention, induction of autoproteolytic cleavage of the heterologous polypeptide is performed by diluting the fusion polypeptide under conditions which promote refolding. Thereby the inactive fusion polypeptide is refolded and thus activated.

In a particularly preferred embodiment, the solubilizate is diluted with an arginine-containing buffer so that the final concentration of arginine is up to 1.0 M, preferably 0.4-0.6 M. Alternatively, dilution is also possible by dialysing the solubilized inclusion bodies against an appropriate arginine-containing cleavage buffer.

The temperature of the reaction solution for the cleavage is, for example, between 0° C. and 30° C. The temperature can preferably be 10° C.-20° C.

The pH of the reaction solution is, for example, 5.0-9.0. The pH is preferably 7.0-8.0, in particular 7.0-7.5. Most preferably the pH is 7.4.

Where appropriate, the reaction solution contains DTT in a concentration of 0.5-100 mM. The DDT concentration is preferably about 5.5 mM.

The protein concentration in the reaction solution during the cleavage can be, for example, in the region of 20-150 μg/ml. The protein concentration is preferably less than 40 μg/ml.

The reaction solution can contain tris/HCl in a concentration of, for example, up to 1.5M during the cleavage. The tris/HCl concentration is preferably between 0.4M and 1.2M.

The reaction solution can contain glycerol in a concentration range of for example between 0.2 and 1%. More preferably the glycerol concentration is 5%.

Also, the reaction solution can contain EDTA in a range of about 1-3 mM EDTA. Prefealy the EDTA concentration is 2 mM.

Other buffer systems are also possible in place of arginine-containing and/or tri/HCl-containing buffers.

In a particularly preferred embodiment, the pH in the cleavage buffer is 7.4, the temperature during the cleavage is 10° C.-20° C., and the cleavage buffer contains about 10 mM DTT as reducing agent, 0.5M NaCl, 5% glycerol, and 2 mM EDTA.

Finally, the heterologous polypeptide which has been cleaved from the fusion polypeptide is isolated in a manner known per se.

In another preferred embodiment of the present invention, induction of autoproteolytic cleavage of the heterologous polypeptide is performed by binding the fusion polypeptide to an affinity chromatographic system, with its autoproteolytic part in an inactive form, and subsequent application of a refolding buffer. In particular, in a first step the fusion polypeptide is bound to the chromatographic system. Binding is maintained while conditions are changed such, that the autoproteolytic part of the fusion polypeptide regains its activity. The polypeptide of interest is cleaved and eluted while the autoproteolytic part of the fusion polypeptide remains bound to the chromatographic system.

In a particularly preferred embodiment of the present invention the affinity chromatographic system is a column, and the fusion polypeptide is inactivated by denaturation. Therefore reactivation of the autoproteolytic activity is induced by application of refolding buffer and thus refolding of the fusion polypeptide.

In a particularly preferred embodiment of the present invention, refolding is conducted in a buffer with the following composition: 0.5M NaCl, 20 mM sodium phosphate, 5% glycerol, 2 mM EDTA, 10 mM DTT 0.01% Brij, pH 7.4.

As used herein the following terms shall have the meanings described below:

The term "heterologous polypeptide of interest" means a polypeptide which is not naturally cleaved by an autoprotease $N^{pro}$ of Pestivirus from a naturally occurring fusion polypeptide or polyprotein. Examples of heterologous polypeptides are industrial enzymes (process enzymes) or polypeptides with pharmaceutical, in particular human pharmaceutical, activity.

The term "fusion polypeptide" refers to polypeptides consisting of two or more polypeptides. In particular herein fusion polypeptides can comprise an affinity tag, an autoproteolytic part, preferably an autoprotease, and the polypeptide of interest.

The term "polypeptide of interest" refers to the polypeptide to be produced with a homogenous N-terminus.

According to the present invention an expression vector can be used, which encodes the polypeptide of interest as the part of the fusion polypeptide which is to be cleaved off autoproteolytically. In accordance with the present invention, a variety of polypeptides of interest can be produced by use of such an expression vector. For example, the polypeptide of interest is one, that exerts pharmacological activity and can for example be selected from the group consisting of an interferon, an interleukin, a growth hormone, a growth factor, a cytokine, an enzyme, an enzyme inhibitor, an antibody and an antibody fragment, and the like, for example interferon alpha 2A, interferon alpha 2B, interleukin-3, interleukin-6, human growth hormone, (pro)insulin, insulin like growth factor, granulocyte-colony stimulating factor, granulocyte macrophage-colony stimulating factor, macrophage-colony stimulating factor, Interferon beta 1, bovine somatropin, porcine somatropin, interleukin 11, interleukin-2, a Fab-fragment, and small peptides such as calcitonin, parathyroid hormone (PTH), or a glucagon, CD 40 ligand soluble form, plasminogen activator, sex steroid binding protein, epidermal growth factor, tissue factor extra cellular domain.

In addition the polypeptide of interest can be any other kind of polypeptide in particular a polypeptide which is especially suited for analytical methods, e.g. Green Fluorescent Protein.

In the expression vector to be employed in the process according to the present invention, the fusion polypeptide is operably linked to at least one expression control sequence. Expression control sequences are, in particular, promoters (such as the lac, tac, T3, T7, trp, gac, vhb, lambda pL or phoA promoter), ribosome binding sites (for example natural ribosome binding sites which belong to the abovementioned promoters, cro or synthetic ribosome binding sites), or transcription terminators (for example rrnB T1T2 or bia).

The vector may also contain sequences encoding fusion domains, as described below, that are present at the N-terminal end of the fusion polypeptide and that are required for its binding to the affinity chromatography system, e.g. polyamino acids like polylysine or, for immunoaffinity chormatography, so-called "epitope tags", which are usually short peptide sequences for which a specific antibody is available. Well known epitope tags for which specific monoclonal antibodies are readily available include FLAG, Influenza virus haemagglutinin (HA), and c-myc tags.

In a preferred embodiment of the present invention, the expression vector is a plasmid.

A bacterial host cell to be employed in the process according to the present invention can be selected, for example, from the group of the following micro organisms: Gram-negative bacteria such as *Escherichia* species, for example *E. coli*, or other Gram-negative bacteria, for example *Pseudomonas* sp., such as *Pseudomonas aeruginosa*, or *Caulobacter* sp., such as *Caulobacter crescendos*, or Gram-positive bacteria such as *Bacillus* sp., in particular *Bacillus subtilis*. *E. coli* is particularly preferred as host cell.

As used herein the term "transformed host cell" shall refer to a cell containing a vector coding for a heterologous polypeptide.

The bacterial host cell, i.e. the expression strain, is cultivated in accordance with microbiological practice known per se. The strain is generally brought up starting from a single colony on a nutrient medium, but it is also possible to employ cryo-preserved cell suspensions (cell banks). The strain is generally cultivated in a multistage process in order to obtain sufficient biomass for further use.

On a small scale, this can take place in shaken flasks, it being possible in most cases to employ a complex medium (for example LB broth). However, it is also possible to use defined media (for example citrate medium). For the cultivation, a small-volume pre-culture of the host strain (inoculated with a single colony or with cell suspension from a cryo-culture) is grown, the temperature for this cultivation not generally being critical for the later expression result, so that it is possible routinely to operate at relatively high temperatures (for example 30° C. or 37° C.). The main culture is set up in a larger volume (for example 500 ml), where it is in particular necessary to ensure good aeration (large volume of flask compared with the volume of contents, high speed of rotation). Since it is intended that expression take place in the form of insoluble inclusion bodies, the main culture will in most cases also be carried out at relatively high temperature (for example 30° C. or 37° C.). Inducible systems are particularly suitable for producing inclusion bodies (for example with trp, lac, tac or phoA promoter). After the late logarithmic phase has been reached (usually at an optical density of 0.5 to 1.0 in shaken flasks), in these cases the inducer substance (for example indoleacrylic add, isopropyl β-D-thiogalactopyranoside=IPTG) is added and incubation is continued for 1 to 5 hours. During this time, most of the N$^{pro}$ fusion polypeptide is deposited as inclusion bodies in the bacterial cytoplasm. The resulting cells can be harvested and processed further.

On a larger scale, the multistage system consists of a plurality of bioreactors (fermenters), it being preferred to employ defined nutrient media in this case in order to be able to improve the process engineering control of the process. In addition, it is possible greatly to increase biomass and product formation by metering in particular nutrients (fed batch). Otherwise, the process is analogous to the shaken flask. For example, a preliminary stage fermenter and a main stage fermenter are used, the cultivation temperature being chosen similar to that in the shaken flask. The preliminary stage fermenter is inoculated with a so-called inoculum which is generally grown from a single colony or a cryoculture in a shaken flask. Good aeration and a sufficient inducer concentration must also be ensured in the fermenter—and especially in the main stage thereof. The induction phase must, however, in some cases be made distinctly longer compared with the shaken flask. The resulting cells are once again delivered for further processing.

In the process according to the present invention, the inclusion bodies are isolated from the host cell in a manner, known per se.

For example, after the fermentation has taken place, the host cells are harvested by centrifugation, micro fitration, flocculation or a combination thereof, preferably by centrifugation. The wet cell mass is disintegrated by mechanical, chemical or physical means such as high pressure homogenizer, beads mills, french press, hughes press, osmotic shock, detergents, enzymatic lysis or a combination thereof. Preferably, disruption of the cells takes place by high pressure homogenization. In the favoured case that the recombinant fusion polypeptide is deposited as inclusion bodies, the inclusion bodies can be obtained for example by means of high-pressure dispersion or, preferably, by a simple centrifugation at low rotor speed. The inclusion bodies are separated by centrifugation or microfiltration or a combination thereof. The purity in relation to the desired polypeptide of interest can then be improved by multiple resuspension of the inclusion bodies in various buffers, for example in the presence of NaCl (for example 0.5-1.0 M) and/or detergent (for example Triton X-100). Preferably the purity of the inclusion body preparation is improved by several washing steps with various buffers (e.g. 0.5% Deoxycholate followed by two times 1 M NaCl solution—and finally distilled water). This usually results in removal of most of the foreign polypeptides in the inclusion bodies.

As used herein the term "solubilization" shall refer to the process necessary to dissolve the inclusion bodies. Solubilization results in a monomolecular dispersion of the polypeptides with minimum intra- and inter-molecular interactions.

A preferred way of solubilization of inclusion bodies within the scope of the present invention, is conducted by suspension in 50 mM Tris/HCl, 8 M urea, pH 7.3, adding a reducing agent, e.g. 50 mM DTT, 4-8M Guanidinium.HCl or Guanidinium SCN, to prevent oxidation of eventually present cysteine residues. Where necessary it is possible to remove potentially insoluble material, for example by centrifugation.

In the case that the inactive fusion polypeptide is produced soluble within the cell, the clarified cell homogenate is subjected to the further work up described above for the solubilized inclusion bodies, except for the step of dilution since the cell homogenate is already diluted.

In a preferred embodiment, the solubilizate is diluted with a Tris/HCl containing buffer so that the final concentration of Tris/HCl is up to 1.5 M, preferably 0.4-1.2 M. Alternatively, dilution is also possible by dialysing the solubilized inclusion bodies against an appropriate Tris/HCl containing cleavage buffer. Tris/HCl can be replaced by other salts eg. 0.2-1.5 M NaCl if an appropriate buffer substance is added eg. 20 mM sodium phosphate.

The temperature of the reaction solution for the cleavage is, for example, between 0° C. and 30° C. The temperature can preferably be 10° C.-20° C.

The pH of the reaction solution is, for example, 5.0-9.0. The pH is preferably 7.0-8.0, in particular 7.0-7.5. Most preferably the pH is 7.4.

Where appropriate, the reaction solution contains DTT in a concentration of 0.5-100 mM. The DDT concentration is preferably about 10 mM.

The protein concentration in the reaction solution during the cleavage can be, for example, in the region of 20-150 μg/ml. The protein concentration is preferably less than 40 μg/ml.

The reaction solution can contain arginine in a concentration of, for example, up to 1.0M during the cleavage. The tris/HCl concentration is preferably between 0.4M and 0.6M.

The reaction solution can contain glycerol in a concentration range of for example between 0.2 and 30%. More preferably the glycerol concentration is 5%.

Also, the reaction solution can contain EDTA in a range of about 1-3 mM EDTA. Preferably the EDTA concentration is 2 mM.

Other buffer systems are also possible in place of arginine-containing and/or tris/HCl-containing buffers.

In a particularly preferred embodiment, the pH in the cleavage buffer is 7.4, the temperature during the cleavage is 10° C.-20° C., the cleavage buffer contains about 10 mM DTT as reducing agent 0.5M NaCl, 20 mM sodium phosphate 5% glycerol and 2 mM EDTA.

Finally the heterologous polypeptide which has been cleaved from the fusion protein is isolated in a manner known per se.

The present invention is described further with reference to the following examples, which are illustrative only and non-limiting. In particular, the examples relate to preferred embodiments of the present invention.

EXAMPLES

With the present invention it is possible to express and produce a wide variety of recombinant proteins (or "polypeptides of interest"), especially such proteins which are problematic to express in usual systems, e.g. proteins with toxic effects on the host cells, proteins which are insoluble or have low solubility, proteins which have other solubility disadvantages (e.g. shorter proteins). The present derivatives also show—in the form of specific fusion constructs or specific activation conditions improvements in cleavage rates, expression rates, overall production rates. Moreover, expression in inclusion bodies with the present constructs show advantageous results for the above mentioned problems (see e.g. example 11).

For example, small proteins have generally low expression rates in E. coli, because they are rapidly degraded in bacterial cells; the constructs according to the present invention allow elevated expression levels (see example 14).

Examples 1, 3, 4, 5, 8 and 9 describe the production of proinsulin utilizing different aspects of the process according to the present invention. The sequence of proinsulin is given below in SEQ ID NO 6, forming the non-bold part of the sequence. In the following for convenience proinsulin is sometimes referred to as insulin.

Example 1

Production of a Heterologous Polypeptide of Interest (Insulin) by Refolding, using the $N^{pro}$-Derivative with SEQ ID NO 5 (EDDIE)

1.1 Generation of Derivatives
1.1.1 Mutational PCR
From the construct containing the DNA sequence for $N^{pro}$-pro-insulin (SEQ ID NO 6):

ATGGAACTCAATCATTTCGAACTGCTCTACAAAACTAGCAAGCAAAAACC
TGTTGGCGTTGAAGAGCCGGTCTACGATACTGCAGGTCGTCCTCTTTTTG
GGAATCCGTCCGAAGTGCACCCCCAGTCAACCCTCAAGCTTCCCCATGAC
CGCGGACGCGGTGACATTCGTACAACGCTGCGCGATCTGCCTCGTAAAGG
CGATTGTCGCTCTGGAAACCACCTAGGTCCGGTGTCGGGCATTTACATTA
AACCAGGTCCCGTCTATTACCAAGACTACACTGGTCCGGTTTACCATCGT
GCACCTCTGGAATTCTTTGATGAAGCTCAATTTTGCGAAGTGACTAAACG
TATTGGCCGTGTAACCGGTTCGGACGGGAAACTGTACCACATCTACGTGT
GCGTTGATGGCTGTATCCTGCTGAAACTCGCGAAGCGCGGAACCCCTCGC
ACCCTGAAATGGATCCGTAACTTCACTAACTGTCCACTGTGGGTCACTAG
TTGCTTCGTTAACCAACATCTGTGCGGTTCACACCTTGTGGAAGCCCTGT
ATCTGGTGTGTGGCGAACGCGGATTCTTTTATACCCCGAAAACGCGGCGC
GAAGCCGAAGATCTTCAGGTTGGTCAAGTGGAACTGGGCGGAGGTCCGGG
AGCCGGAGCCTGCAACCGCTGGCGCTTGAAGGGTCGCTGCAAAAACGCG
GTATTGTTGAACAGTGCTGTACCTCCATCTGCTCTCTGTATCAGCTGGAA
AACTACTGCAATTAATAA that is custom-synthesized and inserted into pUC119 (NCBI #U07650: National Centre for Biotechnology Information Plasmid Database, National Library of Medicine, Building 38A, Bethesda, Md. 20894, USA) by Operon Biotechnologies Inc. (1000 Atlantic Avenue, Suite 108 Alameda, Calif. 94501, USA). From this construct the the required $N^{pro}$-sequence, indicated in bold, is amplified by PCR using the following primer pair $N^{pro}$-F-Ndel, (SEQ ID NO 20) and $N^{pro}$-R-Sall, (SEQ ID NO 21) and inserted via the newly created restriction sites for Ndel and Sall (bold letters, table 1 below) Into the vector pET30a (#69909-3, 2002-2003 catalogue, Novagen, CN Biosciences Inc., Merck KgaA, Darmstadt, Germany) creating S-Np-6H-pET30a. From S-Np-6H-pET30a the $N^{pro}$ sequence is amplified in by two standard 50 μl PCR reactions: one with 50 pmol $N^{pro}$-F-Ndel primer (SEQ ID NO 20) and 50 pmol of one reverse mutation primer selected from Table 1, (SEQ ID NO 8, 10, 12, 14, 16, 18), 5 units Taq DNA-polymerase (# GC 002004, catalog 2004 Genecraft, Treskow Straβe 10, D-48163 Münster, Germany), 1×PCR buffer (# GC 002006 catalog 2004, Genecraft and 20 nmol each dNTP mixture (# GC 013004, catalog 2004, Genecraft); the second with 50 pmol $N^{pro}$-R-Sall primer (SEQ ID NO 21) and 50 pmol of one forward mutation primer, selected from Table 1, (SEQ ID NO 7, 9, 11, 13, 15, 17) 5 units Taq DNA-polymerase, 1×PCR buffer and 20 nmol each dNTP mixture. PCR reaction takes place in a heated lid thermocycler using the following program: 94° C. for 3 min; 25 cycles: 94° C. for 30 sec. 54° C. for 30 sec, 68° C. for 1 min; final incubation at 68° C. for 7 min.

1.1.2 Amplification of Mutant by PCR
The mutation primers given in Table 1 are used to introduce the respective amino acid changes. One-hundredth of both PCRs is combined and amplified in a standard 50 μl PCR reaction with 50 pmol $N^{pro}$-F-Ndel primer (SEQ ID NO 20) and 50 pmol $N^{pro}$-R-Sall primer (SEQ ID NO 21), as described above. Free primers are removed by QIAquick PCR Purification Kit (Qiagen GmbH, Qiagen Strasse 1, D 40724 Hilden, Cat. Nr. 28104, Quiagen product guide 2005)

according to the manufacturers recommendations. The PCR fragments are inserted via the NdeI and SalI restriction sites into vector pET30a. The construct is then used for the next mutational step. This is done in a number of consecutive steps to introduce the amino acid changes necessary to create the desired $N^{pro}$ derivative. In the case of this example the process is repeated six times. The respective amino acid exchanges are indicated in table 1. The outcoming plasmid of each step is controlled by DNA sequence analysis as described (see 4.1) The mutations I155T and F158T are introduced by a single PCR reaction with the primer pair $N^{pro}$-F-NdeI (SEQ ID NO 20) and 3'_I155T, F158T (SEQ ID NO 19) and the resulting PCR product is inserted via the NdeI and SpeI restriction sites into S-Np—H-pET30a. The combination of all eleven amino acid changes results in EDDIE-6H-pET30a, where EDDIE stands for the mutant of the autoprotease $N^{pro}$ of CSFV with SEQ ID NO 5.

TABLE 1

Mutation primers with corresponding amino acid changes:

| | | |
|---|---|---|
| 5'_C112E | SEQ ID NO 7: | GCT CAA TTT GAG GAA GTG ACT AAA CG |
| 3'_C112E | SEQ ID NO 8: | CGT TTA GTC ACT TCC TCA AAT TGA GC |
| 5'_C134E | SEQ ID NO 9: | CAT CTA CGT GGA GGT GAG TGG C |
| 3'_C134E | SEQ ID NO 10: | GCC ATC AAC CTC CAC GTA GAT G |
| 5'_C138E | SEQ ID NO 11: | GTT GAT GGC GAG ATC CTG CTG |
| 3'_C138E | SEQ ID NO 12: | CAG CAG GAT CTC GCC ATC AAC |
| 5'_A109T, V114T | SEQ ID NO 13: | CTG GAA TTC TTT GAT GAA ACC CAA TTT GAG GAA ACC ACT AAA CGT ATT GG |
| 3'_A109T, V114T | SEQ ID NO 14: | CCA ATA CGT TTA GTG GTT TCC TCA AAT TGG GTT TCA TCA AAG AAT TCC AG |
| 5'_RB3E, G54D, R57E | SEQ ID NO 15: | CAT GAC CGC GGA GAA GAT GAC ATT GAA ACA ACG CTG C |
| 3'_R53E, G54D, R57E | SEQ ID NO 16: | GCA GCG TTG TTT CAA TGT CAT CTT CTC CGC GGT CAT G |
| 5'_L143Q | SEQ ID NO 17: | GAT CCT GCT GAA ACA GGC GAA GCG CGG AAC |
| 3'_L143Q | SEQ ID NO 18: | GTT CCG CGC TTC GCC TGT TTC AGC AGG ATC |
| 3'_I155T, F158T | SEQ ID NO 19: | GCA ACT AGT GAG CCA CAG TGG ACA GTT AGT GGT GTT ACG GGT CCA TTT CAG G |
| $N^{pro}$-F-NdeI | SEQ ID NO 20: | CGC GAC ATA TGG AAC TCA ATC ATT TCG AAC-3 |
| $N^{pro}$-R-SalI | SEQ ID NO 21: | CGC AGA GAT GTT GGT CGA CGC TGC AAC TAG TG |

1.2 Construction of Plasmid

This process is conducted analogous to the one described under 4.1.

1.3 Transformation of Host Cells

This process is conducted analogous to the one described under 4.2 below.

1.4 Expression and Fermentation

These processes are conducted analogous to the one described under 4.3 below.

1.5 Cleavage 1 ml of over night culture of host cells transformed as described in 4.2, with construct 6H-EDDIE-SDDIns-pET30a (for construction see 4.1) is transferred into 100 ml M9-KAN medium (50 mM Na2HO4, 20 mM KH2PO4, 10 mM NaCl, 20 mM NH4Cl, 1 mM MgSO4, 0.4% w/v Glucose, 50 µg/ml Kanamycin), incubated at 37° C. and 225 rpm to an OD of 0.5 and induced for expression with 1 mM IPTG at 37° C. for 2 h. Cells are spun down at 2500 g for 15 min. The pellet is suspended in 8 ml lysis-buffer (20 mM $Na_2HPO_4$, 75 mM NaCl, 5 mM EDTA, 2 mM $MgCl_2$), transferred into a pre-cooled press chamber and incubated at 1380 bar for 5 min. The valve is opened slowly and 500 µl aliquots poured drop by drop (2-4 drops/10 sec) into 1.5 ml tubes. The homogenate is spun for 15 min at 19000 g and 4° C., the supernatant discarded and the pellet suspended in 30 µl lysis-buffer (or $H_2O$). 500 µl Guanidinium HCl-solution (5 M Guanidinium HCl, 120 mM Tris pH 7.3, 25 mM DTT) are added and incubated for 40 min at room temperature. 10 µl are transferred into a clean reaction tube for TCA-precipitation (IB control), another 10 µl are transferred into a clean tube for in-vitro renaturation by 1:50 dilution with 490 µl refolding buffer (0.5M NaCl, 5% glycerol, 2 mM EDTA, 10 mM DTT, pH 7.4) for 40 min at RT followed by TCA-precipitation. The TCA precipitates are spun down, the SN discarded, the pellet dissolved in 10 µl 1×SDS-PAGE probe buffer and the success of renaturation and cleavage analyzed by SDS-PAGE. The gel is stained with Coomassie Brilliant Blue R250 (Fluka cat n. 27816, Laborchemlkalien und analytische Reagentien 2005/2008, Fluka Chemie GmbH, industriestrasse 25, CH-9471 Buchs, Switzerland), the bands of uncleaved fusion polypeptides and cleaved autoprotease are quantified by densitometry based on measurement of absorption of white light by the stain and amount of cleavage is calculated.

Example 2

Determination of Solubility

The pellet of an 800 ml culture of E. coli BL21 (DE3) transformed with EDDIE-6H-pET30a (for construction see 1.1.2) is prepared as described under 4.3. The pellet is suspended in 40 ml/g lysis puffer (20 mM $Na_2HPO_4$, 75 mM NaCl, 5 mM EDTA, 2 mM $MgCl_2$, 10 mM 2-Mercaptoethanol pH 8). Lysis of the cells is achieved by two passages through pressure cell (1380 bar). After incubation for 15 min. with 1% Triton X-100 (solubilized in 5 ml/g lysis puffer) the cell homogenate is centrifuged with 25000 g for 45 min, the supernatant discarded and the inclusion bodies (IB) stored at −20° C. Inclusion bodies are dissolved to 1.3 ml/g IB in Guanidinium chloride solution (5 M GuCl, 120 mM Tris, 25 mM DTT, pH 7.5) incubated for 3.5 h at room temperature and centrifuged with 25000 g for 15 min. The supernatant is diluted to 30 ml/g IB in refolding puffer (0.4 M Tris, 10 mM DTT, 2 mM EDTA, 5% Glycerol, 7.3 pH), incubated over night at room temperature, centrifuged and sterile filtered. The $N^{pro}$ derivative is purified by ion exchange chromatography on an SP Sepharose column with a volume of 50 ml.

The column is equilibrated with 3 CV of 0.4 mM Tris pH 7.3 and after application of the refolding solution washed with 150 mM NaCl 20 mM $Na_2HPO_4$, pH 7.5. Elution is carded out with 3 CV 600 mM NaCl, 20 mM $Na_2HPO_4$, 5% Glycerol, pH 7.5. Fractions 8 and 9 (8.5 ml each) containing the protein are combined and concentrated by membrane filtration (Amicon Centricon plus-20, # UFC2LGC24, product catalogue 2004, Millipore Corporation, 290 Concord Rd. Billerica, Mass. 01821, USA) using centrifugation (30 min 805 g) and the resulting solution is subjected to a second concentration step (Amicon Microcon YM-10, #42407, product catalogue 2004, Millipore Corporation) for 30 min at 17000 g and room temperature. After 72 hours the concentrated solution is centrifuged (10 min, 17000 g, room temperature), the pellet dissolved in 10 µl 1×SDS-PAGE probe buffer and applied to SDS gel-electrophoresis. 10 µl of the supernatant are combined with 10 µl 2×SDS-PAGE probe buffer and applied to SDS gel-electrophoresis. After electrophoresis the bands are stained with Coomassie Brilliant Blue R250, quantified as described (2) and the amount of precipitated material is calculated.

Example 3

Production of a Heterologous Polypeptide of Interest (Insulin) by Refolding, using One of the $N^{pro}$-Derivatives with SEQ ID NO 2, 3 or 4, Respectively The different steps of the process are performed analogous for each of the three derivatives with SEQ ID NO 2, 3 or 4. The outcome for these derivatives is according to the results achieved with the derivative with SEQ ID NO 5 (see example 1).

3.1 Generation of Derivatives
3.1.1 Mutational PCR
This process is conducted analogous to the one described under 1.1.1.
3.1.2 Amplification of Mutant by PCR
This process is conducted analogous to the one described under 1.1.2.
3.2 Construction of Plasmid
This process is conducted analogous to the one described under 4.1.
3.3 Transformation of Host Cells
This process is conducted analogous to the one described under 4.2 below.
3.4 Expression and Fermentation
These processes are conducted analogous to the one described under 4.3 below.
3.5 Cleavage
This process is conducted analogous to the one described under 1.5. Solubility and cleavage efficiency can be tested using the techniques disclosed under 1.5 and example 2.

Example 4

Production of a Heterologous Polypeptide of Interest (Insulin) by on Column Refolding, Using the $N^{pro}$-Derivative with SEQ ID NO 5 (EDDIE)

In the following "EDDIE" indicated the mutant of the naturally occurring autoprotease $N^{pro}$ of CSFV with the sequence according to SEQ ID NO 5.

For this experiment the construct pET30-6H-EDDIE-SDD-Ins is used to express the fusion polypeptide 6H-EDDIE-SDD-Ins. This fusion polypeptide comprises an n-terminally 6xhistidine tagged mutant form of the pestiviral autoprotease $N^{pro}$, SEQ ID NO 5, followed by a SDD-linker (serine, aspartic acid, aspartic acid) and the sequence of pro-insulin.

4.1 Construction of Plasmids

The DNA sequence for $N^{pro}$-pro-insuline (SEQ ID NO 6) is custom-synthesized and inserted into pUC119 (NCBI #U07650; National Center for Biotechnology Information Plasmid Database, National Library of Medicine, Building 38A, Bethesda, Md. 20894, USA) by Operon Biotechnologies, Inc. (1000 Atlantic Avenue, Suite 108 Alameda, Calif. 94501, USA).

From this construct the $N^{pro}$-sequence (indicated in bold) which is required is amplified by PCR using the following primer pair: $N^{pro}$-F-Ndel (SEQ ID NO 20) and Ins-R-Sall (SEQ ID NO 22), (5'-CTT TCG TCG ACT TAT TAA TTG CAG TAG TTT TC-3') and the resulting fragment inserted via the newly created restriction sites for Ndel and Sall (bold letters) into the vector pET30a. Transformation (see 4.2) into E. coli strain DH5alpha (#10643-013, Invitrogen catalogue 2003, Invitrogen Life Technologies Corporation, 1600 Faraday Avenue, PO Box 6482 Carlsbad, Calif. 92008), isolation of plasmid DNA from selected clones and DNA sequence analysis verifies S-Np-Ins-pET30a. From EDDIE-6H-pET30a (see for construction under 1.1.2) EDDIE (SEQ ID NO 5) is amplified by PCR using the following primer pair: 6H-$N^{pro}$-F-Ndel (SEQ ID NO 23), (5'-CTC TCA TAT GCA TCA CCA TCA TCA TCA CGA ACT CAA TCA TTT CGA ACT GCT C-3' and $N^{pro}$-R-Sall (SEQ ID NO 21) and the resulting fragment used to replace $N^{pro}$ via restriction sites for Ndel and Spel (bold letters) in the construct S-Np-Ins-pET30a creating 6H-EDDIE-Ins-pET30a. To create a suitable cleavage site for $N^{pro}$ autoprotease the pro-insulin sequence is amplified from plasmid 6H-EDDIE-Ins-pET30a by PCR using the following primer pair: SDDIns-F-Spe (SEQ ID NO 24) (5'-GTA ACT AGT TGC AGC GAT GAC TTC GTT AAC CAA CAT CTG TGC-3') and Ins R Sall, (SEQ ID NO 22) and the resulting fragment used to replace the pro-insulin sequence via restriction sites for Spel and Sall (bold letters) in the construct 6H-EDDIE-Ins-pET30a to create 6H-EDDIE-SDDIns-pET30a. The sequences of the constructs are verified by DNA sequencing according to standard techniques.

4.2 Transformation

Electrocompetent cells are prepared from one liter of bacterial culture (grown at 37° C. and 225 rpm to $OD_{800}$=0.5). The cell suspension is cooled on ice for 15 min (continuous agitation) pelleted (4° C., 2500 g, 10 min) and the supernatant removed. The remaining pellet is resuspend in one liter of deionized water at 4° C., spun down (4° C., 2500 g, 10 min) again and washed 2 times in 50 ml de-ionized water (4° C.) with intermittent centrifuging steps (4° C. 2500 g, 10 min). The pellet is finally washed with 60 ml 10% sterilized glycerol solution (4° C.) pelleted (4° C., 2600 g, 10 min) and resuspended in 2.6 ml 10% sterilized glycerol solution (4° C.), frozen and stored in 40 µl aliquots at −80° C. One aliquot of electrocompetent calls is thawed on ice, 1 µl of ligation reaction containing 5 ng DNA added and transferred without air bubbles to an electroporation cuvette with 1 mm electrode gap. Electroporation takes place with a BIO-RAD Gene Pulser™ (Bio-Rad Laboratories Inc., 2000 Alfred Nobel Drive, Hercules, Calif. 94547, USA; cat n. 1652077, Life Science Research Products 1998) including BIO-RAD pulse controller (Bio-Rad Laboratories Inc., 2000 Alfred Nobel Drive, Hercules, Calif. 94547, USA; cat n. 1652098, Life Science Research Products 1998) set to 1.5 kV, 25 µF, 200 Ohms with a time constant longer than 4.4 ms whereby a plasmid constructed as described under 4.1 is transferred into the cell. Immediately thereafter 180 µl TY-broth (1.0% w/v Peptone, 0.7% w/v Yeast extract, 0.25% w/v NaCl) is added and the suspension transferred to a sterile 14 ml plastic tube and incubated for 30 min (37° C., 225 rpm). The suspension is then plated on selecton medium. After incubation over night at 37° C. colonies are picked, transferred to 2 ml TY-broth and incubated over night at 37° C. and 225 rpm. 1 ml of the overnight culture is used for plasmid preparation by standard methods and the plasmid preparation subjected to restriction analysis and DNA sequencing. After verification by sequence analysis the plasmid is used for further transformation in expression strains by the method described herein.

4.3 Expression and Fermentation 10 ml of an over night expression culture of cells transformed as described above under 4.2 are diluted by 10 with TY-medium (see 1.1.2) and incubated for 30 minutes at 37° C., 225 rpm, followed by induction of protein expression with 1 mM IPTG (Isopropyl-thiogalactoside) for 2 hours at 37° C., 225 rpm. Cells are harvested by centrifugation at 2500 g for 10 minutes and the pellet is resuspended in 8 ml lysis buffer (20 mM $Na_2HPO_4$, 75 mM NaCl, 5 mM EDTA, 2 mM $MgCl_2$, pH 8.0). The suspension is then transferred into a precooled pressure cell and incubated at 1380 bar for 5 minutes. After that the valve is slowly opened and the suspension of disrupted cells is poured drop by drop (2-4 drops/10 seconds) into a clean collection tube. After a second passage through the pressure cell the suspension is divided into aliquots of 500 µl and inclusion bodies are isolated by centrifugation at 4° C., 20000 g for 30 minutes and stored at −20° C. (supernatant is removed before freezing).

4.4 On Column Cleavage of Insulin

One of these aliquots is resuspended in 30 µl $H_2O$ and subsequently dissolved by adding 500 µl of 5M guanidine hydrochloride. After incubation for 40 min at room temperature the inclusion bodies that are dissolved are then applied onto a 500 µl column filled with an immobilized metal affinity matrix, (Quiagen GmbH, Quiagen Strasse 1, D 40724 Hilden, Cat. Nr 30210). After application the column is washed with 5 column volumes (CV) of 5M guanidine hydrochloride and renaturation of the mutated $N^{pro}$ is induced by rapid buffer exchange to refolding buffer (20 mM sodium phosphate pH 7.3. 500 mM NaCl, 5% glycerine, 2 mM EDTA). Refolding buffer is applied until no guanidine hydrochloride is detectable in the flow through, afterwards the column is sealed. The sealed column is incubated for at least 80 minutes, then SDD-Ins is washed out, simply by applying 1 CV of refolding buffer.

Example 5

Production of a Heterologous Polypeptide of Interest (Insulin) by on Column Refolding, Using the $N^{pro}$-Derivative with SEQ ID NO 2, 3 or 4, Respectively For this experiment a construct analogous to that described in example 4 is used. This fusion polypeptide comprises an N-terminally 6xhistidine tagged mutant form of the pestiviral autoprotease $N^{pro}$, (SEQ ID NO 2,3,4 respectively), followed by an SDD-linker (serine, aspartic acid, aspartic acid) and the sequence of pro-insulin.

5.1 Construction of Plasmids

The construction of the plasmids is performed analogous to the process described under 4.1.

5.2 Transformation

The transformation of the host cells is performed analogous to the process described under 4.2.

5.3 Expression and Fermentation

The expression and fermentation is performed analogous to the process described under 4.3.

5.4 On Column Cleavage of Insulin

The on column cleavage of insulin is performed analogous to the process described under 4.4 with similar results.

Example 6

Production of a Heterologous Polypeptide of Interest (Domain D of Protein A from *Staphylococcus aureus*) by Refolding, Using the $N^{pro}$-Derivative with SEQ ID NO 5 (EDDIE)

For this experiment the construct pET30-EDDIE-sSpA-D is used to express the fusion protein EDDIE-sSpA-D. This fusion protein comprises a mutant form of the pestiviral autoprotease $N^{pro}$ with (SEQ ID NO 5), (EDDIE) followed by domain D of *Staphylococcus aureus* protein A.

6.1 Construction of Plasmid

A codon optimized DNA sequence for domain D of *Staphylococcus aureus* protein A, (SEQ ID NO 25):

```
GCAGACGCACAACAGAATAAGTTTAACAAAGACCAGCAGAGCGCATTCTA

CGAAATTCTGAACATGCCGAATCTGAATGAGGAACAACGTAATGGCTTTA

TTCAGTCTTTAAAAGACGACCCATCTCAGAGCACCAACGTTCTGGGCGAA

GCAAAGAAACTGAACGAATCTCAGGCACCAAAA
``` is assembled by PCR of six partially overlapping oligonucleotides

```
SPAD1Spe (SEQ ID NO 26):
ATATACTAGTTGCGCAGACGCACAACAGAATAAGTTTAACAAAGACCAGC

AG;

SpA-D2 (SEQ ID NO 27):
CATGTTCAGAATTTCGTAGAATGCGCTCTGCTGGTCTTTGTTAAACTTA

T;

SpA-D3 (SEQ iD NO 28):
CATTCTACGAAATTCTGAACATGCCGAATCTGAATGAGGAACAACGTAA

T;

SpA-D4 (SEQ ID NO 29):
GGGTCGTCTTTTAAAGACTGAATAAAGCCATTACGTTGTTCCTCATTCA

G;

SpA-D5 (SEQ ID NO 30):
TCAGTCTTTAAAAGACGACCCATCTCAGAGCACCAACGTTCTGGGCGAA

G;

SpA-D6 Sal (SEQ ID NO 31):
TTTTGGTGCCTGAGATTCGTTCAGTTTCTTTGCTTCGCCCAGAACGTT
``` in a 50 µl PCR reaction with 5 units Taq DNA-polymerase (Biotherm Kat. Nr. GC-002, Genecraft GmbH, Raiffeisenstr. 12, 59348 Lüdinghausen, Germany), 1×PCR buffer (delivered with Biotherm, Genecraft), 20 nmol each dNTP mixture (GC-013-002, Genecraft) using the following program: initial incubation at 94° C. 3 min, 25 cylces of 94° C. 30 sec. 54° C. 30 sec, 68° C. 30 sec. and final incubation at 68° C. for 7 min. 1 µl of the first PCR is directly amplified in a standard 50

µl PCR reaction with 50 pmol of 5'- and 3'-flanking primers (SpA-D1 Spe and SpA-D6_Sal). The success of the gene assembly procedure is analyzed by 1% agarose gel electrophoresis in a manner known per se. The purified sSpA-D PCR product is digested with SpeI and SalI and ligated into dephosphorylated pET30-EDDIE-6Ha (for construction see under 1.1.2) according to standard methods. Transformation into *E. coli* strain DH5alpha (#10643-013, Invitrogen catalogue 2003, Invitrogen Life Technologies Corporation, 1600 Faraday Avenue, PO Box 6482 Carlsbad, Calif. 92008), is performed analogous to the procedure described under 4.2. Isolation of plasmid DNA from selected clones in a manner known per se and DNA sequence analysis as known in the art verify pET30-EDDIE-sSpA-D.

6.2 Transformation

The transformation of the host cells is performed analogous to the process described under 4.2.

8.3 Expression and Fermentation

The expression and fermentation is performed analogous to the process described under 4.3.

8.4 Cleavage of Domain D of Protein A from *Staphylococcus aureus*

Cleavage of domain D of protein A from *Staphylococcus aureus* is performed analogous to the process described under 1.5.

Example 7

Generation of the Derivative According to SEQ ID NO 32 (EDDIEN35T,T158S; Asparagine 35 Replaced by Threonine, and Threonine 158 Replaced by Serine)

Starting from the derivative comprising SEQ ID NO 5 (EDDIE) a derivative wherein in addition N35 is replaced by T, and T 158 is replaced by S is constructed by mutational PCR as described in 1.1.2. Two consecutive steps are performed using the primer pairs: 5'_N35T (5'CTC TTT TTG GGA CCC CGT CCG AAG TG3) and 3'_N35T (5'CAC TTC GGA CGG GGT CCC AAA AAG AG3') as well as E 5'_T158S (5'GGA CCC GTA ACA GCA CTA ACT GTC C3') and E 3'_T165S (5'GGA CAG TTA GTG CTG TTA CGG GTC C3'). The resulting fragment is used to replace EDDIE in the vector 6H-EDDIE-Ins-pet30a via the NdeI and SpeI restriction sites. The DNA sequence of derivative EDDIEN35T,T158S is verified by DNA sequencing.

Example 8

Production of a Heterologous Polypeptide of Interest (Proinsulin), Using the N$^{pro}$-Derivative with SEQ ID NO 33

8.1 Generation of the Derivative According to SEQ ID NO 33:

1 ng of EDDIEN35T158S-Ins-pet30a is used for random mutagenesis with the GeneMorph PCR II random mutagenesis kit (Stratagene, 11011 North Torrey Pines Road, La Jolla, Calif. 92037, USA, Cat #200550 catalog 2005). In detail, 5 µl 10× buffer (GeneMorphII), 1 µl 40 mM dNTP-mix (GeneMorphII), 2.5 µl (103 ng each) primer-mix IF-Np-Nde-F (5'-AAG GAG ATA TAC ATA TGG AAC TCA ATC ATT TCG AAC TG-3') and IF-Np-Ins-Spe-R (5'-TAA CGA AGC AAC TAG TGA CCC ACA GTG GAC AGT TAG T-3') 1 µl Mutazyme® (GeneMorphII), 1 ng EDDIEN35T, T158S-Ins-pet30a, A. dest. ad 50 µl. This mixture is subjected to the following PCR-Program: 1 min 94° C.; step 1 to 30:30 sec 94° C., 30 sec 55°, 1 min 72° C.; final step: 10 min 72° C.; hold 10° C. The reaction with the given amount of DNA leads to 4 mutations per N$^{pro}$ gene in average. After PCR the reaction mix is purified using the QIAquick PCR Purification Kit (Qiagen GmbH, Qiagen Strasse 1, D 40724 Hilden, Cat #28104, Qiagen product guide 2005) according to the manufacturer's recommendations.

8.2 Construction of Plasmids

The construction of the plasmids is performed analogous to the process described under 4.1. The fragments generated according to 8.1 are used to replace the N$^{pro}$ gene in the plasmid EDDIE-Ins-pet30a via the NdeI and SpeI restriction sites thus creating a random mutagenesis pool of N$^{pro}$ derivatives.

8.3 Transformation

The transformation of the host cells is performed analogous to the process described under 4.2.

8.4 Expression and Fermentation

The expression and fermentation is performed analogous to the process described under 4.3.

8.5 Cleavage Analysis

Cleavage analysis is conducted as described under 1.5.

Example 9

Production of a Heterologous Polypeptide of Interest (Proinsulin) Using the N$^{pro}$-Derivative According to SEQ ID NO 32

Alternatively the derivative according to SEQ ID NO 32 can be used in the process described above. The derivative is produced as described in example 7.

The steps described under 8.2 to 8.5 are performed analogous for the derivative with SEQ ID NO 32.

Example 10

10.1. Generation of Threonine-Serine Derivatives of EDDIE

To further increase to polarity of EDDIE the amino acids Threonine (T) in positions 109, 114, 155, 158 and Glutamine (Q) 143 are replaced by Serine (S) by gene assembly. To this the gene for EDDIE is split into the following set of 15 overlapping oligonucleotides and assembled by PCR as described in 6.1:

Primer List

```
e1;
CAATCATTTCGAACTGCTCTACAAAACTAGCAAGCAAAAACCTGTTGGCG

TTGAAGAGCCG e2;
GGAATCCGTCCGAAGTGCACCCCCAGTCAACCCTCAAGCTTCCCCATGAC

CGCGGAG e3;
GCTGCGCGATCTGCCTCGTAAAGGCGATTGTCGCTCTGGAAAC e4;
GGGCATTTACATTAAACCAGGTCCCGTCTATTACCAAGACTACACTGGTC

CGGTTTACCATC e5agc;
GTGCACCTCTGGAATTCTTTGATGAAAGCCAATTTGAGGAAAGCACTAAA

CGTATTGGCCGTGTAAC
```

-continued e6;
CTGTACCACATCTACGTGGAGGTTGATGGCGAGATCCTGCTG e7agc;
CCCCTCGCACCCTGAAATGGAGCCGTAACAGCACTAACTGTCCACTGTGG
GTC e8;
GTAGAGCAGTTCGAAATGATTGAGTTCCATATGTCGCG e9;
CACTTCGGACGGATTCCCAAAAAGAGGACGACCTGCAGTATCGTAGACCG
GCTCTTCAACGCCAACAG e10;
GAGGCAGATCGCGCAGCGTTGTTTCAATGTCATCTTCTCCGCGGTCATGG
GGAAG e11;
CTGGTTTAATGTAAATGCCCGACACCGGACCTAGGTGGTTTCCAGAGCGA
CAATCGCCTTTAC e12;
CAAAGAATTCCAGAGGTGCACGATGGTAAACCGGACCAGTG e13;
CTCCACGTAGATGTGGTACAGTTTCCCGTCCGAACCGGTTACACGGCCAA
TACGTTTAG e14agc;
CCATTTCAGGGTGCGAGGGGTTCCGCGCTTCGCGCTTTTCAGCAGGATCT
CGCCATCAAC e15;
CGCAGAGATGTTGGTCGACGCTGCAACTAGTGACCCACAGTGGACAGTTA
G The resulting fragment is used to replace the N$^{pro}$ gene in s-Np-6H-pet30a via the NdeI and SpeI restriction sites. The DNA sequence of derivative 92 is verified by DNA sequencing. Transformation into bacterial cells and expression and fermentation in done as described under 4.2 and 4.3. Cleavage analysis is conducted as described under 1.5.

| no. | Amino acid changes in N$^{pro}$ derivative |
|---|---|
| 92 | R53E, G54D, R57E, A109S, C112E, V114S, C134E, C138E, L143S, I155S, F158S |

SEQ ID 92:
(1)-MELNHFELLYKTSKQKPVGVEEPVYDTAGRPLFGNPSEVHPQSTLK

LPHDRGEDDIETTLRDLPRKGDCRSGNHLGPVSGIYIKPGPVYYQDYTGP

VYHRAPLEFFDESQFEESTKRIGRVTGSDGKLYHIYVEVDGEILLKSAKR

GTPRTLKWSRNSTNCPLWVTSC-(168).

EDDIE 143 derivatives:

To exchange the amino add S143 with a number of other polar amino acids (D, G, H, K, N, Q) oligonucleotide e14 is repaced by the degenerated oligonucleotide e14vaw containing the nucleotide composition VAW for the codon in position 143 (V:ACG; W:AT). Since e14vaw is a reverse oligonucleotide it contains the reverese complementary triplett WTB.

e14vaw; CCATTTCAGGGTGCGAGGGGTTCCGCGCTTCGCWTBTTTCAGCAGGATCTCGCCATCAAC

The same gene assembly process and insertion in s-Np-6H-pet30a resulted in the mutants described in table of mutants.

Transformation into bacterial cells and expression and fermentation in done as described under 4.2 and 4.3. Cleavage analysis is conducted as described under 1.5.

Table of Mutants:

| no. | Amino acid changes in N$^{pro}$ derivative |
|---|---|
| 95 | R53E, G54D, R57E, A109S, C112E, V114S, C134E, C138E, L143N, I155S, F158S |
| 96 | R53E, G54D, R57E, A109S, C112E, V114S, C134E, C138E, L143D, I155S, F158S |
| 97 | R53E, G54D, R57E, A109S, C112E, V114S, C134E, C138E, L143H, I155S, F158S |
| 98 | R53E, G54D, R57E, A109S, C112E, V114S, R120C, C134E, C138E, L143Q, I155S, F158S |

SEQ ID 95:
(1)-MELNHFELLYKTSKQKPVGVEEPVYDTAGRPLFGNPSEVHPQSTLK

LPHDRGEDDIETTLRDLPRKGDCRSGNHLGPVSGIYIKPGPVYYQDYTGP

VYHRAPLEFFDESQFEESTKRIGRVTGSDGKLYHIYVEVDGEILLKNAKR

GTPRTLKWSRNSTNCPLWVTSC-(168).

SEQ ID 96:
(1)-MELNHFELLYKTSKQKPVGVEEPVYDTAGRPLFGNPSEVHPQSTLK

LPHDRGEDDIETTLRDLPRKGDCRSGNHLGPVSGIYIKPGPVYYQDYTGP

VYHRAPLEFFDESQFEESTKRIGRVTGSDGKLYHIYVEVDGEILLKDAKR

GTPRTLKWSRNSTNCPLWVTSC-(168).

SEQ ID 97:
(1)-MELNHFELLYKTSKQKPVGVEEPVYDTAGRPLFGNPSEVHPQSTLK

LPHDRGEDDIETTLRDLPRKGDCRSGNHLGPVSGIYIKPGPVYYQDYTGP

VYHRAPLEFFDESQFEESTKRIGRVTGSDGKLYHIYVEVDGEILLKHAKR

GTPRTLKWSRNSTNCPLWVTSC-(168).

SEQ ID 98:
(1)-MELNHFELLYKTSKQKPVGVEEPVYDTAGRPLFGNPSEVHPQSTLK

LPHDRGEDDIETTLRDLPRKGDCRSGNHLGPVSGIYIKPGPVYYQDYTGP

VYHRAPLEFFDESQFEESTKRIGCVTGSDGKLYHIYVEVDGEILLKQAKR

GTPRTLKWSRNSTNCPLWVTSC-(168).

Construction of sNp-FVN-6H-pet30a

To insert the peptide FVN-6H containing the first three amino acids of insulin and the 6His tag (FVNVDKLAAALE-HHHHHH) N$^{pro}$ is amplified from plasmid sNp-6H-pet30a with the primer pair sNp FVN R Sal (5'-GAG AGT CGA CGT TAA CGA AGC AAC TAG TGA CCC ACA GTG-3') and N$^{pro}$-F-Ndel primer (SEQ ID NO 20) by a standard PCR reaction and the resulting fragments used to replace N$^{pro}$-6H via the restriction sites NdeI and SalI by standard procedures creating plasmid sNp-FVN-6H-pet30a.

Example 11

Production of a Heterologous Polypeptide of Interest (Double Domain D of *Staphylococcus aureus* Protein A) Using the N$^{pro}$-Derivative According to SEQ ID NO 5 (EDDIE) and the N$^{pro}$-Derivative Containing the Amino Acid Substitutions C134E and C138E 11.1 Construction of pET30-6H-EDDIE-sSpA-D-sSpA-D The domain D of *Staphylococcus aureus* protein A generated by gene assembly (see Example 6) is amplified by PCR from pET30-EDDIE-sSpA-D (6.1) by use of the primer pair (SpA-D1; GCAGACGCACAACAGAATAAGTTTAAC and SpA-D6; TTTTGGTGCCTGAGATTCGT-TCAGTTTCTTTGCTTCGCCCAGAACGTT) using essentially the same PCR reaction conditions as in Example 6 and subjected to a domain assembly process. In a first step single domains are linked together by PCR with a link-primer pair (SpA-Dlink2RC; CTGCTGGTCTTTGTTAAACTTATTCT-GTTGTGCGTCTGCTTTTGGTGCCTGAGATTCGTT C and SpA-DLink; GAACGAATCTCAGGCACCAAAAG-CAGACGCACAACAGAATAAGTTTAA-CAAAGACCAGC AG). In this PCR reaction the link-primer concentration is reduced to 0.5 pmol, while the that of template (single domain D) is elevated to 10-25 pmol. The reverse-link-primer attaches a reverse complementary sequence of the 5' end to the 3'end of the monomer and the forward link-primer attaches a reverse complementary sequence of the 3' end to the 5' end, respectively. These new 5' and 3' linking-ends of domain D anneal with the complementary 3' and 5' linking-sequences of another domain D, respectively. Hence, many units of one specific domain are linked together producing synthetic genes with multiple repeats of domain D. To allow subsequent isolation and cloning and to get rid of the 5' and 3' ends attached during the first PCR reaction, anchor and restriction sites are incorporated by a second PCR with the adaptor-primer pair: fish-R-Sal-SpA; GATCTTCAGGTTGGTCAAGTGGGTC-GACTTATTTTGGTGCCTGAGATTCGTTCAGT TTC and fish2-F-Spe-SpA; gagaGAAGAgTGGCTACTGTAgAG ACTAGTTGCGCAGACGCACAACA-GAATAAGTTTAAC. One tenth of the first PCR reaction is directly added to the second PCR mixture containing 0.5 pmol adaptor-primer. The reaction products are separated by agarose gel electrophoresis and the fragments containing the double domain D extracted from the gel by QIAquick Gel Extraction Kit. The double domain D genes are amplified by PCR using 50 pmol of anchor-primers (fish2-F; gagaGAA-GAgTGGCTACTGTAgAG and fish-R; GATCTTCAGGT-TGGTCAAGTGG), purified by gel electrophoresis and digested with SpeI/SalI and cloned into pET30-6H-EDDIE-Ins digested with the same enzymes, which results in a replacement of the sequence of proinsulin with the double domain D sequence, thereby giving rise to the construct pET30-6H-EDDIE-sSpA-D-sSpA-D (fusion of EDDIE with with double domain D of *Staphylococcus aureus* protein A).

11.2 Expression of pET30-6H-EDDIE-sSpA-D-sSpA-D

Transformation into bacterial cells, expression and fermentation is done as described under 4.2 and 4.3. Cleavage analysis conducted as described under 1.5 reveales, that besides of the cleaved N$^{pro}$-EDDIE protein and the double domain D the majority of the uncleaved fusion protein (about 90 percent) is also found in the soluble fraction. Therefore it is considered to use the N$^{pro}$ derivative containing the amino acid substitutions C134E and C138E which showed very low in vivo cleavage rate.

11.3 Construction of pET$^{30}$-N$^{pro}$C134E/C138E-sSpA-D-sSpA-D

The N$^{pro}$C134E/C138E DNA sequence is amplified with the primer pair IF Np-Nde-F (5'AAGGAGATATACATATG-GAACTCAATCATTTCGAACTG3') and IF Np SpAD-Spe-R (5'CGTCTGCGCAACTAGTGACCCACAGTG-GACAGTTAGT3') cut with the restriction enzymes NdeI/SpeI and inserted into the vector pET30-6H-EDDIE-sSpA-D-sSpA-D digested with NdeI/SpeI thereby replacing 6H-EDDIE with N$^{pro}$C134E/C138E and giving rise to the construct pET30-N$^{pro}$C134E/C138E-sSpA-D-sSpA-D.

11.4 Expression of Npro C134E, C138E-sSpA-D-sSpA-D

Transformation into bacterial cells, expression and fermentation is done as described under 4.2 and 4.3. Cleavage analysis conducted as described under 1.5 reveales, that most of the uncleaved fusion protein was found in the insoluble fraction after cell disruption via French Press. This result shows that by use of different N$^{pro}$ derivatives the amount of in vivo cleavage rates and direction of the expression of the fusion proteins into inclusion bodies can be controlled. Moreover, refolding of N$^{pro}$C134E/C138E-sSpA-D-sSpA-D shows besides almost zero in vivo cleavage still approx. 33% cleaved products in vitro.

Example 12

Production of a Heterologous Polypeptide of Interest (JAC, a Direct Target of Oncogenic Transcription Factor Jun) Using the N$^{pro}$-Derivative with SEQ ID NO 5 (EDDIE)

12.1 Construction of 6H-EDDIE-JAC

The gene for JAC, a direct target of oncogenic transcription factor Jun which is involved in cell transformation and tumorigenesis, is amplified from a cDNA clone pAC01(Markus Harti et. al. JAC, a direct target of oncogenic transcription factor Jun, is involved in cell transformation and tumorigenesis. PNAS 98, 13601-13606, 2001) by PCR with the oligonucleotide primers JAC1(GATCACTAGTTGCATGC-CCAACGGAGG) and JAC2 (GATCGTCGACTTAGTTGCCACAGCCACA) containing the SpeI and SalI restriction sites according to the protocol described in 1.1.1. The resulting fragment is used to replace the insulin gene from 6H-EDDIE-Ins-pet30a to create 6H-EDDIE-JAC-pet30a. The sequences of the constructs are verified by DNA sequencing according to standard techniques.

Transformation into bacterial cells and expression and fermentation in done as described under 4.2 and 4.3. Cleavage analysis is conducted as described under 1.5.

Example 13

Production of a Heterologous Polypeptide of Interest (Interferon Alpha 1, IFNA1) Using the N$^{pro}$-Derivative with SEQ ID NO 5 (EDDIE)

13.1 Construction of 6H-EDDIE-sIFNA1-pet30a:

The gene encoding IFNA1 (gene bank accession number NM_024013) is assembled by PCR as described (10.1) using the following oligonucleotide set:

IFNA1-1
ATA TAC TAG TTG CAT GGC ACC GAC CTC T

IFNA1-2
AAA TGG CAT TGC AGC TTA ACA GAA CTA ATG CCG TCA

GAA AGG CAG AGG TCG GTG CCA TGC

IFNA1-3
GTT CTG TTA AGC TGC AAT GCC ATT TGT TCT TTA GGC

TGC GAT CTG CCA CAA ACC CAC TCT

IFNA1-4
CAT TTG TGC CAG CAG ACG TAA GGC ACG CGT ATG GGC

CAG AGA GTG GGT TTG TGG CAG ATC

IFNA1-5
CTT ACG TCT GCT GGC ACA AAT GCG TCG CAT TAG CCC

ATT CTC TTG TCT GGA TCA TCG CCG

IFNA1-6
TGG TTA CCA CCA AAG GCC TCG TGC GGA GAG CCG AAA

TCA CGG CGA TGA TCC AGA CAA GAG

IFNA1-7
GAG GCC TTT GGT GGT AAC CAA GTC CAA AAG GCC CAG

GCA ATG GCC TTA GTG CAG GAG ATG

IFNA1-8
TGC CCT CCG TGC TGA ATA ACT GAA AGG TCT GTT GCA

GCA TCT CAT GCA CTA AGG CCA TTG

IFNA1-9
GTT ATT CAG CAC GGA GGG CAG CGC AGC GGC CTG GAA

TGA AAG CTT ACT GCA CCA ATT TTG

IFNA1-10
TCT AAA TCG CGC AGT TGT TGG TCC AGA CCG GTA CAA

AAT TGG TGC AGT AAG CTT TCA TTC

IFNA1-11
ACC AAC AAC TGC GCG ATT TAG AAG CCT GCG TCA TGC

AAG AAG CGG GCT TAG AAG GTA CCC

IFNA1-12
ATA CTT GCG CAC CGC TAA AAT AGA GTC TTC CTC TAA

TAA TGG GGT ACC TTC TAA GCC CGC

IFNA1-13
CTC TAT TTT AGC GGT GCG CAA GTA TTT CCA TCG TTT

AAC CTT ATA CTT ACA GGA AAA ATC

IFNA1-14
ACG ATC TCC CAT GCG CAC GGG CTG TAA GAT TTT TCC

TGT AAG TAT AAG GTT AAA CGA TGG

IFNA1-15
GTG CGC ATG GGA GAT CGT TCG CGC GGA GGT CAT GCG

TAG CTT CAG CAG CTC TCG TAA TCT

IFNA1-16
ATA TGT CGA CTT ATT CCT TCT TAC GCA GAC GGT CTT

GCA GAT TAC GAG AGC TGC TGA AGC

The resulting fragment is digested with the restriction enzymes SpeI and SalI and used to replace the insulin gene from 6H-EDDIE-Ins-pet30a to create 6H-EDDIE-sIFNA1-pet30a. The sequences of the constructs are verified by DNA sequencing according to standard techniques.

Transformation into bacterial cells and expression and fermentation in done as described under 4.2 and 4.3. Cleavage analysis is conducted as described under 1.5.

Example 14

Production of a Heterologous Polypeptide of Interest (Hepcidin), Using 6H-EDDIE-Ins The DNA sequence of hepcidin is amplified by PCR from the template "huhep in pCR2.1" (S. Ludwiczek, Department of Internal Medicine, University of Innsbruck) using the primer pair "Hep25 F Spe" (5'-TCG ACT AGT TGC GAC ACC CAC TTC CCC ATC-3')/"Hep R Sal" (5'-ATC GTC GAC TTA CGT CTT GCA GCA CAT CCC AC-3').

The resulting DNA fragment is digested by SpeI/SalI and cloned into pET30-6H-EDDIE-Ins digested with the same enzymes, which results in a replacement of the sequence of proinsulin with the hepcidin25 sequence, hereby giving rise to the construct pET30-6H-EDDIE-Hep25 (fusion of EDDIE with mature hepcidin).

Transformation of pET30-6H-EDDIE-Hep25 into *E. coli* BL21-CodonPlus(DE3)-RIL (Cat. Nr. 230245, Stratgene, 11011 N. Torrey Pines Road, La Jolla, Calif. 92037, USA, 2004 Catalog) bacterial cells, expression and fermentation is done as described under 4.2 and 4.3. After that cell-harvest, cell-disruption, isolation of IBs, renaturation and cleavage analysis is conducted as described under 1.5. The results show about 80% cleavage of EDDIE-Hepcidin25.

The invention claimed is:

1. A modified autoprotease N$^{pro}$ of classical swine fever virus (CSFV), wherein one or more cysteine residues of the naturally occurring autoprotease N$^{pro}$ selected from the group consisting of C112, C134, and C138 is replaced by a glutamic acid residue, and wherein the amino acid positions for replacement are numbered according to the amino acid sequence set forth in SEQ ID NO:1.

2. The modified autoprotease N$^{pro}$ according to claim 1, comprising the amino acid sequence set forth in SEQ ID NO:2.

3. The modified autoprotease N$^{pro}$ according to claim 1, wherein in addition to the replaced cysteine residues at least one basic amino acid residue is replaced by an acidic amino acid residue.

4. The modified autoprotease N$^{pro}$ according to claim 3, wherein in addition to the replaced cysteine residues the following amino acid replacements are made: R53E, G54D, R57E, and L143Q.

5. The modified autoprotease N$^{pro}$ according to claim 4, comprising the amino acid sequence set forth in SEQ ID NO:3.

6. The modified autoprotease N$^{pro}$ according to claim 2, wherein in addition to the replaced cysteine residues at least one basic amino acid residue is replaced by an acidic amino acid residue.

7. The modified autoprotease N$^{pro}$ according to claim 1, wherein in addition to the replaced cysteine residues at least one hydrophobic amino acid residue is replaced by a hydrophilic residue.

8. The modified autoprotease $N^{pro}$ according to claim 7, wherein in addition to the replaced cysteine residues the following amino acid replacements are made: A109T, V114T, I155T, and F158T.

9. The modified autoprotease $N^{pro}$ according to claim 8 comprising the amino acid sequence set forth in SEQ ID NO:4.

10. The modified autoprotease $N^{pro}$ according to claim 2, wherein in addition to the replaced cysteine residues at least one hydrophobic amino acid residue is replaced by a hydrophilic residue.

11. The modified autoprotease $N^{pro}$ according to claim 1, wherein in addition to the replaced cysteine residues the following amino acid replacements are made: R53E, G54D, R57E, A109T, V114T, L143Q, I155T, and F158T.

12. The modified autoprotease $N^{pro}$ according to claim 11 comprising the amino acid sequence set forth in SEQ ID NO:5.

13. The modified autoprotease $N^{pro}$ according to claim 2, wherein in addition to the replaced cysteine residues the following amino acid replacements are made: R53E, G54D, R57E, A109T, V114T, L143Q, I155T, and F158T.

14. The modified $N^{pro}$ according to claim 11, wherein in addition the following amino acid replacements are made: N35T and T158S.

15. The modified autoprotease $N^{pro}$ according to claim 14 comprising the amino acid sequence set forth in SEQ ID NO:32.

16. The modified autoprotease $N^{pro}$ according to claim 14, wherein in addition the following amino acid replacements are made: A28E, S71F, and R150H.

17. The modified autoprotease $N^{pro}$ according to claim 16 comprising the amino acid sequence set forth in SEQ ID NO:33.

18. The modified autoprotease $N^{pro}$ according to claim 1 wherein in addition to the replaced cysteine residues at least one of the following amino acids is replaced with a different amino acid: R53, G54, R57, A109, V114, L143, I155, and F158.

19. The modified autoprotease $N^{pro}$ according to claim 1 wherein in addition to the replaced cysteine residues at least one of the following amino acid replacements are made: R53E, G54D, R57E, A109S, V114S, L143Q, L143N, L143D, L143S, L143H, I155S, and F158S.

20. The modified autoprotease $N^{pro}$ according to claim 1 comprising the amino acid sequence set forth in SEQ ID NO:34.

21. The modified autoprotease $N^{pro}$ according to claim 1 comprising the amino acid sequence set forth in SEQ ID NO:35.

22. The modified autoprotease $N^{pro}$ according to claim 1 comprising the amino acid sequence set forth in SEQ ID NO:36.

23. The modified autoprotease $N^{pro}$ according to claim 1 comprising the amino acid sequence set forth in SEQ ID NO:37.

24. The modified autoprotease $N^{pro}$ according to claim 1 comprising the amino acid sequence set forth in SEQ ID NO:38.

25. A process for the recombinant production of a heterologous polypeptide of interest, comprising,
  (i) cultivation of a bacterial host cell which is transformed with an expression vector which comprises a nucleic acid molecule which codes for a fusion polypeptide, the fusion polypeptide comprising the modified autoprotease $Ne^{pro}$ according to claim 1, and a second polypeptide which is connected to the first polypeptide at the C-terminus of the first polypeptide in a manner such, that the second polypeptide is capable of being cleaved from the fusion polypeptide by the autoproteolytic activity of the first polypeptide, said second polypeptide being a heterologous polypeptide, wherein cultivation occurs under conditions which cause expression of the fusion polypeptide and formation of corresponding cytoplasmic inclusion bodies,
  (ii) isolation of the inclusion bodies from the host cell,
  (iii) solubilization of the isolated inclusion bodies,
  (iv) induction of autoproteolytic cleavage of the heterologous polypeptide of interest from the fusion polypeptide, and
  (v) isolation of the cleaved heterologous polypeptide of interest.

26. The process according to claim 22, wherein the fusion polypeptide comprises a modified autoprotease $N^{pro}$, according to any one of claims 2 through 24, 6, 10, and 13.

* * * * *